US008865223B2

(12) United States Patent
Barenholz et al.

(10) Patent No.: US 8,865,223 B2
(45) Date of Patent: *Oct. 21, 2014

(54) BETA-CASEIN ASSEMBLIES FOR MUCOSAL DELIVERY OF THERAPEUTIC BIOACTIVE AGENTS

(75) Inventors: Yechezkel Barenholz, Jerusalem (IL); Dganit Danino, Nesher (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/867,215

(22) PCT Filed: Feb. 11, 2009

(86) PCT No.: PCT/IL2009/000155
§ 371 (c)(1),
(2), (4) Date: Nov. 17, 2010

(87) PCT Pub. No.: WO2009/101613
PCT Pub. Date: Aug. 20, 2009

(65) Prior Publication Data
US 2011/0052703 A1    Mar. 3, 2011

Related U.S. Application Data

(60) Provisional application No. 61/027,633, filed on Feb. 11, 2008, provisional application No. 61/030,005, filed on Feb. 20, 2008.

(51) Int. Cl.
| | |
|---|---|
| A61K 9/14 | (2006.01) |
| A61K 9/16 | (2006.01) |
| A61K 9/50 | (2006.01) |
| A23L 1/305 | (2006.01) |
| A23J 1/22 | (2006.01) |
| A23B 4/03 | (2006.01) |
| A61K 31/665 | (2006.01) |
| A61K 31/415 | (2006.01) |
| A61K 9/00 | (2006.01) |
| A61K 9/107 | (2006.01) |
| A61K 31/573 | (2006.01) |

(52) U.S. Cl.
CPC ............. *A61K 9/00* (2013.01); *A61K 9/1075* (2013.01); *A61K 31/415* (2013.01); *A61K 31/573* (2013.01)
USPC ............. 424/499; 424/489; 426/72; 426/657; 514/100; 514/141; 514/403

(58) Field of Classification Search
None
See application file for complete search history.

(56) References Cited

U.S. PATENT DOCUMENTS

| | | | |
|---|---|---|---|
| 5,173,322 | A | 12/1992 | Melachouris |
| 5,318,793 | A | 6/1994 | Melachouris |
| 5,399,363 | A | 3/1995 | Liversidge |
| 5,405,756 | A | 4/1995 | Naito |
| 5,462,751 | A | 10/1995 | Kossovsky |
| 5,603,930 | A | 2/1997 | Brassart |
| 5,833,953 | A | 11/1998 | Berrocal |
| 6,290,974 | B1 | 9/2001 | Swaisgood |
| 6,503,545 | B1 | 1/2003 | Perlman |
| 6,652,875 | B1 | 11/2003 | Bannister |
| 6,991,823 | B2 | 1/2006 | Augustin |
| 2002/0054914 | A1 | 5/2002 | Morcol |
| 2003/0180367 | A1 | 9/2003 | Parikh |
| 2004/0137071 | A1 | 7/2004 | Unger |
| 2004/0234666 | A1* | 11/2004 | Law et al. ............. 426/580 |
| 2005/0031544 | A1* | 2/2005 | Njemanze .............. 424/9.322 |
| 2007/0104847 | A1 | 5/2007 | O'Mahony |
| 2007/0166368 | A1 | 7/2007 | Singh |
| 2008/0145432 | A1 | 6/2008 | Kakizawa |
| 2009/0029017 | A1 | 1/2009 | Singh |
| 2010/0062073 | A1 | 3/2010 | Beyerinck |
| 2011/0038987 | A1 | 2/2011 | Danino et al. |
| 2011/0052703 | A1 | 3/2011 | Barenholz |

FOREIGN PATENT DOCUMENTS

| | | |
|---|---|---|
| EP | 1348430 | 10/2003 |
| GB | 2041378 | 1/1983 |
| WO | 96/29340 A1 | 9/1996 |
| WO | 00/06108 A1 | 2/2000 |
| WO | 0264112 | 5/2002 |
| WO | 2004000252 | 1/2004 |
| WO | 2007017513 | 1/2007 |
| WO | 2007069272 | 3/2007 |
| WO | 2007/122613 A1 | 11/2007 |
| WO | 2008135852 | 6/2008 |
| WO | 2009101612 | 4/2009 |
| WO | 2009101614 | 4/2009 |

OTHER PUBLICATIONS

Y. Le Graet et al. "Les equilibres mineraux du lait: influence du pH et de la force ionique"; Lait (1993) 73, 51-60.*
Graet et al.; J. Dairy Research (1999) 66, 215-224.*
Bellare et al., (1988) Controlled environment vitrification system: an improved sample preparation technique. Electron Microsc. Technique 10:87-111.
O'Connell J. et al., (2003) Association behavior of beta-casein. Journal of Colloid and Interface Science 258(1): 33-9.

(Continued)

*Primary Examiner* — Jeffrey T Palenik
(74) *Attorney, Agent, or Firm* — Browdy and Neimark, PLLC

(57) ABSTRACT

Nanoparticulate assemblies of isolated beta-casein, are useful for encapsulation of bioactive therapeutic substances, particularly therapeutic agents with poor bioavailability. These nano-sized beta-casein assemblies are preferably formed at pH values which are at least one or more pH units below or above the pI of the protein. Pharmaceutical compositions comprising the beta-casein micelles may be used to administer the agents to the GI tract for treatment of local or systemic conditions. These carriers are stable over a wide temperature range (optionally at least from about 1° C. to at least about 45° C.).

21 Claims, 22 Drawing Sheets

(56) References Cited

OTHER PUBLICATIONS

Pan X. et al., (2007) Simultaneous nanoparticle formation and encapsulation driven by hydrophobic interaction of casein-graft-dextran and beta-carotene. Journal of Colloid and Interface Science 315:456-63.
Portnaya I. et al., (2006) Micellization of bovine beta-casein studied by isothermal titration microcalorimetry and cryogenic transmission electron microscopy. J. Agric. Food Chem. 54:5555-61.
Portnaya I. et al., (2008) Self-assembly of bovine beta-casein below the isoelectric Ph. J Agric Food Chem. 56 (6):2192-8.
Semo E. et al., (2007) Casein micelle as a natural nano-capsular vehicle for nutraceuticals. Food Hydrocolloids 21 (5-6):936-42.
Zhang X. et al., (2005) Chaperone-like activity of beta-casein. Int. J. Biochem. Cell Biol. 37(6):1232-40.
Database Biosis [Online], Biosciences informaiotn service , Philadelphia, PA, US; 1979, Evans MT. et al., The conformation and aggregation of bovine β-casein A. II. Thermodynamics of thermal association and the effects of changes in polar and apolar interactions on micellization, XP002531439 Database accession No. PREV197968060329 abstract & Biopolymers 1979;18(5):1123-1140.
Dalgleish and Law (1988) Sodium caseinates—composition and properties of different preparations. International Journal of Dairy Technology 41(1): 1-4.
Shapira et al., (2012) β-Casein nanoparticle-based oral drug delivery system for potential treatment of gastric carcinoma: stability, target-activated release and cytotoxicity. Eur J Pharm Biopharm 80: 298-305.
Aoki, T. et al., (1989) Incorporation of individual casein constituents into micelles in artificial casein micelles. Nippon Chikusan Gakkaiho 60:583-589.
Bootz, Alexander et al., (2004) Comparison of scanning electron microscopy, dynamic light scattering and analytical ultracentrifugation for the sizing of poly(butyl cyanoacrylate) nanoparticles. Eur J Pharm Biopharm 57(2):369-375.
Brophy, Brigid et al., (2003) Cloned transgenic cattle produce milk with higher levels of beta-casein and kappa-casein. Nat Biotechnol 21(2):157-162.
Christiens, Bart et al., (2002), Tryptophan fluorescence study of the interaction of penetratin peptides with model membranes. Eur J Biochem 269(12):2918-2926.
Cogan et al., Binding affinities of retinol and related compounds to retinol binding proteins. Eur J Biochem 1976;65:71-8.
Farrell, H. M. Jr. et al., (2006), Casein micelle structure: What can be learned from milk synthesis and structural biology?. Current Opinion in Colloid and Interface Science 11:135-147.
Fornier, Monica N. et al., (2007) Increased dose density is feasible: a pilot study of adjuvant epirubicin and cyclophosphamide followed by paclitaxel, at 10- or 11-day intervals with filgrastim support in women with breast cancer. Clin Cancer Res 13(1):223-227.
Forrest, Stephanie A. et al., (2005) Interactions of vitamin D3 with bovine beta-lactoglobulin A and beta-casein. J Agric Food Chem 53(20):8003-8009.
Guo et al., (2003) Casein precipitation equilibria in the presence of calcium ions and phosphates. Colloids and Surfaces B: Biointerfaces 29: 297-307.
Hogan, Sean A. et al., (2001) Microencapsulating Properties of Sodium Caseinate. Journal of Agricultural and Food Chemistry 49:1934-1938.
Horne DS., Casein Interactions: Casting Light on the Black Boxes, the Structure in Dairy Products. Int Dairy 1998;8 (3):171-7.
Horne, David S. (2002) Casein structure, self-assembly and gelation. Current Opinion in Colloid & Interface Science 7(5-6):456-461.
Jubeh, Tareq Taha et al., (2004) Differential adhesion of normal and inflamed rat colonic mucosa by charged liposomes. Pharm Res 21:447-453.
Jubeh, Tareq Taha et al., (2005) Local prevention of oxidative stress in the intestinal epithelium of the rat by adhesive liposomes of superoxide dismutase and tempamine. Mol Pharm 2(1):2-11.
Jubeh, Tareq Taha et al.,(2006) Local treatment of experimental colitis in the rat by negatively charged liposomes of catalase, TMN and SOD. J Drug Target 14(3)155-163.
Karlsson et al., Observations of casein micelles in skim milk concentrate by transmission electron microscopy. LWT—Food Science and Technology 2007; 40(6):1102-7.
Kauf, M. C. W. and Kensinger, R. S. (2002) Purification of porcine beta-casein, N-terminal sequence, quantification in mastitic milk. J Anim Sci 80:1863-1870.
Knepp, W. A. et al., (1993) Synthesis, properties, and intratumoral evaluation of mitoxantrone-loaded casein microspheres in Lewis lung carcinoma. J Pharm Pharmacol 45(10):887-891.
Knoop, Anne Marie et al., (1979) Sub-structure of synthetic casein micelles. Journal of Dairy Research 46:347-350.
Le Graet, Y. and Brule, G. (1993) Effects of pH and ionic strength on distribution of mineral salts in milk. Lait 73:51-60 article in French with summary in English.
Le Graet, Y. et al., (1999) pH-induced solubilization of minerals from casein micelles: influence of casein concentration and ionic strength. J Dairy Res 66:215-224.
Livney D., Experimental report: Comparison of the binding of vitamin D to casein under the conditions of D1 and under the conditions of Livney & Dalgleish, measured by spectrofluorometry, submitted as EP 07 73 6236.6, filed on Oct. 15, 2008.
Mattila, Pirjo et al., (2001), Contents of vitamins, mineral elements, and some phenolic compounds in cultivated mushrooms. Journal of agricultural and food chemistry 49:2343-2348.
Renken, Shelly A. and Warthesen, Joseph J. (1993) Vitamin D stability in milk. J Food Science 58(3):552-556.
Ribadeau Dumas, Bruno et al., (1972) Primary structure of bovine beta casein. Complete sequence. Eur J Biochem 25(3):505-514.
Thomsen et al., (1995) Solid-state magic-angle spinning 31P-NMR studies of native casein micelles. Eur J Biochem 230: 454-459.
Tirosh, Boaz et al., (2009) Transferrin as a luminal target for negatively charged liposomes in the inflamed colonic mucosa. Mol Pharm 6(4):1083-1091.
Weissenboeck, Andrea et al., (2004) Binding and Uptake of Wheat Germ Agglutinin-Grafted PLGA-Nanospheres by Caco-2 Monolayers. Pharm Res 21(10)1917-1923.
Zhang, Liangke et al., (2004) Uptake of folate-conjugated albumin nanoparticles to the SKOV3 cells. Int J Pharm 287 (1-2):155-162.
Zimet et al., Re-assembled casein micelles and casein nanoparticles as nano-vehicles for ω-3 polyunsaturated fatty acids. Food hydrocolloids 2011; 25(5)1 270-6.

* cited by examiner

BETA-CASEIN ASSEMBLIES FOR MUCOSAL DELIVERY OF THERAPEUTIC BIOACTIVE AGENTS

FIELD OF THE INVENTION

The present invention relates to drug carrier compositions comprising beta-casein micelle assemblies for mucosal delivery, which is delivery through a mucosal membrane. The present invention further provides methods of manufacturing same and therapeutic methods utilizing same for mucosal delivery of the drug.

BACKGROUND OF THE INVENTION

Many drugs and agent delivered orally suffer from poor bioavailability due to many drawbacks including poor drug absorption in the gastrointestinal tract (GI), poor stability in the GI and especially in the stomach, low solubility, etc. For all these cases there is an unmet need to overcome these drawbacks in order to improve drug bioavailability so to achieve therapeutic efficacy through effective drug delivery.

Treatment of many diseases including lethal or chronic illnesses often requires daily use of drugs or therapeutic bioactive agents, for example in the form of injection. This can result in non-compliance of the patient due to the discomfort caused by multiple administrations. In addition to being uncomfortable, injection is also expensive. Enteral delivery of such bioactive agents and drugs may provide an advantageous route for administration and may encourage patient compliance. However, oral administration of such molecules is often restricted by acid digestion of the drugs or bioactive compounds in the stomach and digestion in the small intestine. Thus, many systems focus on protecting the encapsulated molecule from degradation, and facilitating the transport of the intact molecule.

Many existing encapsulation systems for enteral delivery of drugs use biocompatible, semi-permeable polymeric capsules, enclosures or membranes, which deliver the drug to the desired release point (typically along the gastrointestinal tract) and then permit release of the drug. Other such systems use Liposomes or other structures to contain the drug. Frequently such systems provide controlled release of the drug, for better therapeutic efficacy, although immediate release is also possible. The material(s) selected for surrounding the drug are selected for compatibility with the active ingredient and desired release properties.

Casein, which accounts for about 80% of milk protein, is organized in micelles. Casein micelles (CM) are designed by nature to efficiently concentrate, stabilize and transport essential nutrients, mainly calcium and protein, for the neonate. All mammals' milk contains casein micelles. Cow's milk contains 30-35 g of protein per liter, of which about 80% is within CM.

CM are usually describe as clusters of unorganized mixture of the main four caseins: $\alpha_{s1}$-casein ($\alpha_{s1}$-CN), $\alpha_{s2}$-CN, β-CN, and κ-CN (molar ratio ~4:1:4:1 respectively (DeKruif and Holt, Advanced Dairy Chemistry-1 Proteins Part A; 3 Fox, P F; McSweeney, P. L. H., Eds.; Kluwer Academic/Plenum Publishers: New York, 2005; 233-276). The caseins are held together by hydrophobic interactions as well as by calcium-phosphate bridges. CM form only at neutral pH and their typical sizes are in the range of 50-500 nm.

Harnessing the remarkable CM natural nano-capsules for nano-encapsulation and stabilization of hydrophobic nutraceutical substances was suggested in the prior art. Semo et al., referred to the incorporation of such CM nano-capsules in dairy products without modifying their sensory properties (Semo E. Food Hydrocolloids 2007, 21; 936-42) and further suggested their use as delivery agents of sensitive health-promoting substances using natural GRAS (generally regarded as safe) ingredients.

PCT Publication WO 2007/122613 described a system based on re-assembled casein micelles for the delivery of hydrophobic biologically active compounds in food and beverages. The teachings relate specifically to the incorporation of such re-assembled casein micelles into low-fat or non-fat dairy products or other food or beverage products without adversely modifying their properties. The taught micelles are composed of sodium caseinate comprising at least the main four casein proteins and are re-assembled at neutral pH. The reassembly of CM is enforced by flow and exposure to high pressure.

U.S. Pat. No. 6,652,875 provides a formulation for the delivery of bioactive agents to biological surfaces comprising at least one isolated and purified casein protein or salt thereof in water. The disclosure relates to particular isolated and purified casein phosphoproteins in the form of casein calcium phosphate complexes intended to remain on the surface of oral cavity tissues or the gastrointestinal tract. Specific particle formation is neither taught nor suggested. Furthermore the taught micelles comprise a casein protein selected from alpha-casein, beta-casein, kappa-casein, and mixtures thereof. This application emphasizes the presence of divalent and trivalent metal ions.

U.S. Patent Application Publication No. 2002/0054914 teaches a calcium phosphate/drug core with casein micelles reconstructed as aggregates around the cores, forming micellar structures, for the delivery of pharmaceutical agents. According to that disclosure, casein molecules are arranged, presumably as micelles, around calcium phosphate particles containing the active drug, and are linked to the therapeutic agent-containing microparticles by mainly calcium phosphate and electrostatic bond interactions.

U.S. Patent Application Publication No. 2009/0029017 provides a protective system for oxidisable lipids by encapsulating them in a complex of casein and whey proteins. The emulsion is reported to stabilize the oxidisable lipid by decreasing its rate of oxidation. The emulsion is further reported to be heat stable which allows it to be heat treated and sterilized. However, the emulsion clearly requires a combination of both types of proteins; furthermore, the effect of low pH values and/or low temperature is not discussed. In fact, the pH is stated to be preferably between 6 and 9, with the upper end of the range even more preferred. Also the complex is stated to be formed by heating to between 70-100 degrees C.

Casein-dextran copolymer nanoparticles encapsulating insoluble β-carotene was disclosed by Pan X. et al. (Journal of Colloid and Interface Science, 2007, 315; 456-63). The nanoparticles contained a casein and β-carotene core surrounded by a dextran shell. The particles were shown to have spherical shape with a size of about 100 nm and are stable in aqueous solution even after long term storage. The casein-dextran nanoparticles were suggested as possible delivery agents for unstable and hydrophobic nutrients and drugs. However the teachings clearly require a casein-dextran copolymer for forming the nanoparticles.

U.S. Pat. No. 5,405,756 discloses acid soluble casein phosphopeptides prepared by enzymatic digestion of intact casein followed by step wise acidification of the digest causing precipitation of acid insoluble molecules. This procedure teaches that caseins tend to precipitate at pH values around the pI of the protein.

The use of beta-casein micelles as nanodelivery vehicles for chemotherapeutic drugs was presented in the 48th Microsymposium of PMM Polymer colloids held in Prague, the Czech Republic, during July 2008, and at a scientific gathering in Hagoshrim Israel December 2008, after the priority date of the application from which the present application claims priority.

There is still an unmet medical need for effective, safe and easy to manufacture delivery systems for improved bioavailability of bioactive ingredients, particularly for small organic molecules with poor solubility or poor absorption or poor stability or potential adverse effects in the GI tract.

SUMMARY OF THE INVENTION

The present invention discloses for the first time the formation of stable nanoparticulate beta-casein assemblies, which are stable at low pH values, contrary to the teachings of the background art. These nano-sized beta-casein assemblies are preferably formed at pH values which are preferably one or more pH units below the pI of the protein. More preferably the beta-casein nano-assemblies are formed at low pH, optionally and preferably at least one and more preferably at least two pH units below the pI of beta-casein (pH=5.3).

Optionally and preferably the nano-assemblies comprise denatured beta-casein micelles, wherein by "denatured" it is meant that the nano-assemblies were formed under acid conditions at least 1 pH unit below the pI of the beta-casein; however it is within the scope of the present invention that the nano-assemblies may then optionally be subjected to higher pH values. Without wishing to be limited by a single hypothesis, it is believed that the resultant micelles are less susceptible to enzyme degradation. These carriers are stable over a wide temperature range (optionally at least from about 1° C. to at least about 45° C.). As a natural food product, this GRAS (generally recognized as safe) protein is biocompatible and biodegradable, which should not elicit immune responses against it.

According to some embodiments, the present invention features a composition comprising micelles formed from an isolated beta-casein under acid conditions below the pI of beta-casein and preferably at least one pH unit, more preferably at least two pH units, below the pI of the beta-casein. The micelles of the composition preferably comprise a majority of beta-casein, optionally at least about 70%, preferably at least about 80%, more preferably at least about 90% and most preferably at least about 95% beta-casein of the casein.

The present invention, in some embodiments, further discloses the use of these assemblies as carriers for the loading of bioactive compounds, particularly drugs and therapeutic compounds. Optionally and preferably, the assemblies are suitable for delivery of a bioactive compound or compounds through or across a mucosal membrane for mucosal delivery. Mucosal delivery preferably includes delivery across any suitable mucosal membrane, which may be selected by one of ordinary skill in the art according to one or more therapeutic factors. The therapeutic factors preferably include but are not limited to the type or characteristic(s) of the bioactive compound(s), the desired therapeutic effect, one or more characteristics of the recipient subject and so forth. Mucosal delivery may optionally include one or more of oral, rectal, nasal or vaginal delivery.

As noted above, it has now been found that these nanoparticulate beta-casein carriers are unexpectedly stable at a wide low-pH range, and at a wide range of temperatures. As a natural, digestible food component, beta-casein is biocompatible, and thus should not elicit immune responses against it. The beta-casein assemblies provide protection to fully or partially encapsulated drugs and therapeutic bioactive agents in the harsh acidic environment of the stomach. The incorporated drug or agent may be any therapeutically effective agent, such as a natural isolated extracted or synthetic chemical or biological agent including small molecules, oligomers, polymers, proteins, enzymes and peptides. The guest agents can be of various character including highly hydrophobic, amphiphilic or even highly polar and/or charged molecules, which can be of various molecular weights. One compound can be encapsulated, as well as several compounds together. The drugs may be encapsulated in the hydrophobic pocket of the protein assemblies or at the interface.

The beta-casein assemblies according to some embodiments of the present invention are further engineered to load bioactive therapeutic agents, and protect the loaded molecules. The interaction with the vehicle increases the solubility of some poorly-soluble drugs. The empty carrier and the loaded system are also stable in a wide temperature range, from at least about 1° C., up to over 40° C., and in acidic pH they are stable for longer times than the empty beta-casein micelles. Moreover, the loaded delivery systems are often stable for longer periods than the unloaded systems. The high stability of the carriers to temperature extremes provides an additional significant advantage, as for many drugs the carrier can be stored for a long time at low temperatures (e.g., 4° C.) then taken orally at ambient temperature. The high stability to such changes in temperature is superior to other existing systems at low pH, as well as to systems at neutral and physiological pH. With some therapeutic agents, precipitation occurs at low temperatures but the re-solubilization occurs within minutes of bringing the system to room temperature, without damage to the therapeutic agent or to bioavailability thereof.

The empty carrier and the loaded system are also stable in a wide ionic strength range from at least about 0.002M to about 0.5M. More typically, from at least about 0.002M to about 0.2M. Even more typically, from at least about 0.002M to about 0.1M.

According to some embodiments of the present invention the amount of the beta-casein in the composition is between about 0.05 and about 50%. More typically, the amount of beta-casein present in the composition is between about 0.2 and about 25%. Even more typically, the amount of beta-casein present in the composition is between about 0.2% and about 10%. Still more typically, the amount of beta-casein present in the composition is between about 0.2% and about 5%. Yet still more typically, the amount of beta-casein present in the composition is between about 0.2 and about 2%. According to some preferred embodiments the beta-casein assemblies of the present invention exclude calcium atoms. Without wishing to be bound by any theory or mechanism of action, beta-casein micellar compositions of the present invention at pH below the beta-casein pI are not held together by calcium-phosphate bridges.

Carrier assemblies as described herein according to some embodiments of the present invention are therefore surprisingly useful for a wide range of classes of drugs which suffer from poor oral or other mucosal membrane absorption, and hence bioavailability, which severely limits their applicability, usage and effectiveness. Such therapeutic agents (also referred to herein as active ingredients) may optionally comprise any type of bulky, large, hydrophobic, insoluble in an aqueous solution and/or at body pH values, and/or pH sensitive material, including without limitation plant alkaloids and the like, drugs with multi-cyclic ring structures (including those that lack polar groups), peptides and proteins, including antibodies and enzymes, or any type of biopolymer, including without limitation oligonucleotides and polynucleotides (including without limitation siRNA molecules and the like). According to preferred embodiments, the agents do not comprise a chemotherapeutic drug, which is any drug having high systemic toxicity for treatment of cancer.

Non-limiting examples of such classes of drugs include non-steroidal anti-inflammatory drugs (NSAID) such as COX-2 inhibitors, ibuprofen, naproxen, diclofenac, indomethacin, piroxicam, etc., anti-resorptive agents such as bisphosphonates, steroids including corticosteroids, antivirals (acyclovir, IUdR, ganciclovir, vidarabine, AZT), steroidal anti-inflammatory drugs (dexamethasone, loteprednol, prednisolone derivatives, etc.), antibiotics (e.g., ampicillin and erythromycin), antifungals (e.g., miconazole), hormones, local anesthetics, analgesics, calcium channel blockers (e.g., Verapamil), prostaglandins and prostacyclins, cholinergics, adrenergic antagonists, anticonvulsants (e.g., phenytoin), antianxiety agents, major tranquilizers, antidepressants, anabolic steroids, estrogens, progesterones, immune suppressants such as cyclosporine, glycosaminoglycans (heparin, heparan, chondroitin sulfate, and low molecular weight derivatives thereof); any type of fluorescent dye, including but not limited to cyanines, indocyanines, or squaraines; antihelminthics, anti-arrhythmic agents, antibacterial agents, anti-viral agents, anti-coagulants, anti-diabetics, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-blockers, cardiac inotropic agents, corticosteroids, diuretics, anti-Parkinsonian agents, gastro-intestinal agents, histamine receptor antagonists, keratolyptics, lipid regulating agents, anti-anginal agents, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids; and combinations thereof, or derivative or salt thereof.

In addition to the above listed therapeutic agents, specific examples of therapeutic agents may optionally comprise one or more of acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eprosartan, ergocalciferol, ergotamine, etodolac, etoposide, famotidine, fenofibrate, fentanyl, fexofenadine, finasteride, fluconazole, flurbiprofen, fluvastatin, fosphenyloin, frovatriptan, furazolidoneu, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, montelukast, nabumetone, nalbuphine, naratriptan, nelfmavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, sodium clodronate, spironolactone, sumatriptan, tacrine, tacrolimus, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, valsartan, venlafaxine, verteporfin, vigabatrin, zafirlukast, zileuton, zolmitriptan, zolpidem, zopiclone, pharmaceutically acceptable salts, isomers, and derivatives thereof, and combinations thereof.

The above description notwithstanding, according to some embodiments of the present invention, the therapeutic agent does not comprise a chemotherapeutic drug as defined above.

However, according to alternative embodiments of the present invention, the therapeutic agent does comprise a chemotherapeutic drug. All chemotherapeutic agents used to treat cancer are associated with severe side effects and toxicity phenomena, most of which are dose dependent. Most anti-infectious agents also demonstrate dose-dependent adverse side effects and toxicity. Therefore, it would be advantageous to be able to reduce these adverse effects by the use of a drug carrier that imparts reduced toxicity to therapeutically active systems. Alternatively, it would also be advantageous to reduce the overall toxic effects of therapeutic agents on a patient's system through minimization of the delivery of the therapeutic, and therefore toxic, component of treatment agents to clinically irrelevant tissue sites.

Non-limiting examples of suitable chemotherapeutic drugs include a taxane (e.g., paclitaxel), vincristine, adriamycin, vinca alkaloids (e.g., vinblastine), anthracyclines (e.g., doxoribicin), epipodophyllotoxins (e.g., etoposide), cisplatin, actinomycin D, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, hrinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid, or combinations or derivative or salt thereof.

However, it should be noted that according to some embodiments, chemotherapeutic drugs are specifically not encompassed within the formulations or compositions of the present invention, such that any of the embodiments described herein may optionally have the proviso that the therapeutic agent does not comprise a chemotherapeutic drug, and more specifically, that the therapeutic agent does not comprise methotrexate or mitoxantrone. Optionally and more preferably, for those embodiments which encompass chemotherapeutic drugs, the micelles are limited to a size in a range below about 300 nm, even more preferably below about 200 nm and most preferably below about 100 nm in diameter.

In terms of selecting the appropriate amount of therapeutic agent to be carried by the micelles (for example contained within, surrounded by and so forth), the amount is preferably effective to treat or prevent any of the conditions, diseases or disorders described herein as appropriate. An amount being effective to provide the desired effect can be readily determined, in accordance with the invention, by administering to a plurality of tested subjects various amounts of the therapeutic loaded onto the micelles and then plotting the physiological response (for example an integrated "SS index" combining several of the therapeutically beneficial effects) as a function of the amount of loaded therapeutic agent. Alternatively, the effective amount may also be determined, at times, through experiments performed in appropriate animal models and then extrapolating to human beings using one of a plurality of conversion methods. As known, the effective amount may depend on a variety of factors such as mode of administration, the age, weight, body surface area, gender, health condition and genetic factors of the subject; other administered drugs; etc.

The assemblies of the present invention can be prepared by adding the drug solubilized in a solvent or cosolvent, e.g., ethanol, to the beta-casein assemblies or micelles at acidic or neutral pH followed by stirring. Typically the amount of ethanol present in the composition or formulation is between 0.05 and about 20%. More typically, between about 0.1 and about 10%. Even more typically, between 0.1 and about 8%. Yet even more typically, between 0.1 and 5%. Alternatively, the assemblies of the present invention can be prepared by dry mixing the drug and beta-casein, and then adding the dry mixture to a buffer whereas the buffer is an acidic buffer or a neutral buffer. This procedure avoids the addition of ethanol.

It is to be explicitly understood that within the scope of the present invention, the compositions may comprise more than one therapeutic agent. For example, each of the therapeutic agents may be mixed with ethanol and then combined with the beta-casein assemblies or micelles at acidic or neutral pH. In alternative embodiments, two or more different therapeutic agents may be combined within a single beta-casein assembly or micelle. In alternative embodiments two or more therapeutic agents may be individually combined with the beta-casein assemblies or micelles and then combined together. In alternative embodiments two or more therapeutic agents may be dry mixed with beta-casein powder and then added to an aqueous solution of acidic or neutral pH. The oral delivery system may optionally be taken in a liquid form, or the liquid system can be further encapsulated within suitable capsules or coated to allow simple oral use, using methods well known in the art of pharmaceutical science.

Beta-Casein constitutes about 38% of the casein in bovine milk. Its primary structure is composed of 209 amino acids, and its molecular mass is 23,946 to 24,097 Da (depending on the genetic variant). It is the most hydrophobic casein because of its large hydrophobic C-terminal domain (based on its primary structure). However, its highly charged N-terminal domain, containing the phosphate center, makes it very amphipathic. The pronounced amphiphilic structure of beta-Casein imparts many properties resembling those of low molecular weight surfactants. Thus, the protein tends to self-assemble under appropriate conditions into well defined micelles of about 15 to about 60 molecules with a critical micelle concentration (CMC) in the range of 0.05-0.2%, depending on temperature, pH, solvent composition and ionic strength (Portnaya I. et al. 2006, J. Agric. Food Chem. 54;5555-61).

The critical micelle concentration (CMC) is defined as the concentration of surfactant (in this case, the beta-casein protein) above which micelles are spontaneously formed. Upon introduction of the protein into the system (such as for example the compositions described herein), the protein will initially partition into the interface, reducing the system free energy by a) lowering the energy of the interface (calculated as area×surface tension) and b) by removing the hydrophobic parts of the surfactant from contacts with water. Subsequently, when the surface coverage by the surfactants increases and the surface free energy (surface tension) has decreased, the surfactants start aggregating into micelles, thus again decreasing the system free energy by decreasing the contact area of hydrophobic parts of the surfactant with water. Upon reaching CMC, any further addition of surfactants typically increases the number of micelles.

These characteristics give micelles composed of at least a majority of beta-Casein proteins an advantage over the prior art casein micelles which size distribution cannot be controlled very well (typical sizes are 50-500 nm in diameter), such that their heterogeneity is large, and encapsulation is likely restricted.

According to at least some embodiments, the micelles of the present invention have a diameter of optionally below about 300 nm, preferably below about 200 nm or more preferably below about 100 nm.

According to some embodiment of the present invention, the composition comprises micelles, wherein the micelles comprise isolated beta-casein prepared at neutral pH, wherein the isolated beta-casein of the micelles is at least about 70% wt/wt of the total casein, wherein the micelles have a diameter of optionally below about 300 nm, preferably below about 200 nm or more preferably below about 100 nm.

The present invention, in at least some embodiments, overcomes precipitation of beta-casein by preferably preparing the micelles at a pH value that is at least about one unit, and more preferably at least about two units, still more preferably more than two pH units below the pI of beta-casein. According to some embodiments of the present invention, the process for preparation of the micelles involves directly introducing the dry beta-casein into a pH at least one or at least two or more pH units below the pI rather than gradual reduction in pH thus avoiding precipitation at pH values close to the pI of the beta-casein.

According to another aspect of the present invention the micelle assemblies may advantageously be dried or lyophilized using any of the methods known in the art. The dried assemblies may conveniently be used as pharmaceutical compositions per se or may be reconstituted in a suitable liquid medium prior to use.

BRIEF DESCRIPTION OF THE DRAWINGS

FIG. 4: (a) SAXS curves of β-casein solutions, obtained for different protein concentrations at pH 2.6 at 4° C. For better visibility, only each fifth experimental point of the scattering curves is shown. The forward scattering intensity was determined by fitting the experimental curves with the IFT routine including desmearing. (b) Aggregation numbers as a function of the concentration, determined from the scattering curves given in a.

DETAILED DESCRIPTION OF SOME EMBODIMENTS

Figure 1:
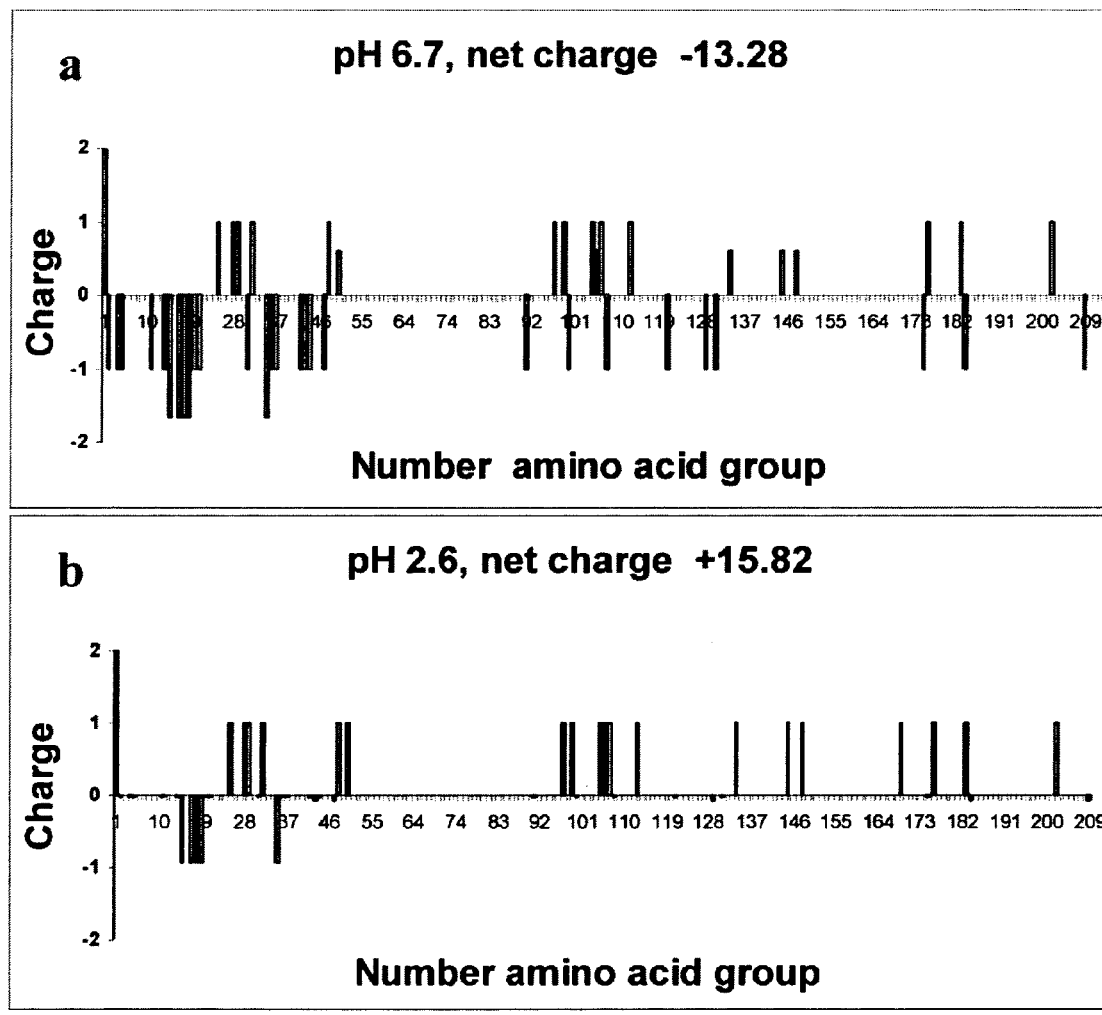
FIG. 1: Distribution of charges along the beta-casein backbone at pH 6.7 (panel a) and pH 2.6 (panel b).

The present invention, in at least some embodiments, provides stable nanoparticulate beta-casein assemblies, which are stable at low pH values, as well as at neutral pH. These nano-sized beta-casein assemblies are formed at pH values which are preferably one or more pH units below the pI of the protein. More preferably the beta-casein nano-assemblies are formed at low pH, optionally and preferably at least one and more preferably at least two pH units below the pI of beta-casein (pH=5.3). According to at least some other embodiments the beta-casein assemblies of the present invention are also formed at neutral pH, preferably between pH 6.5-7.5. These carriers formed at both pH values below the pI of beta-casein as well as at neutral pH are stable over a wide temperature range (optionally at least from about 1° C. to at least about 45° C.).

According to some embodiments, the present invention features a composition comprising assemblies formed from isolated beta-casein or recombinant beta-casein under acid conditions below the pI of beta-casein and preferably at least one pH unit, more preferably at least two pH units, below the pI of the beta-casein. The assemblies of the composition preferably comprise a majority of beta-casein, optionally at least about 70%, preferably at least about 80%, more preferably at least about 90% and most preferably at least about 95% beta-casein.

According to some embodiments, the present invention features a composition comprising assemblies formed from isolated beta-casein or recombinant beta-casein under neutral conditions above the pI of beta-casein and preferably between about pH 6.5 and about pH 7.5. The assemblies of the composition preferably comprise a majority of beta-casein, optionally at least about 70%, preferably at least about 80%, more preferably at least about 90% and most preferably at least about 95% beta-casein.

The present invention, in some embodiments, further discloses the use of these assemblies as carriers for the loading of bioactive compounds, particularly drugs and therapeutic compounds. Micelles can be loaded and carry a broad spectrum of low molecular weight molecules varying in their polarity from highly hydrophobic to highly hydrophilic. This variability allows for very large flexibility and for adapting the details of the formulation for the needs.

For example in some diseases, surfaces of the GI mucosa are negatively charged and therefore will bind favorably particles having positive charged such as beta-casein molecules under acidic pH. The casein micelles loaded with drug will be placed in enteric coated capsules which may optionally be constructed from any suitable enteric polymer, capsules alone or indeed any type of controlled dissolution rate system. For example, the enteric coating optionally and preferably comprises at least one enteric material selected from the group consisting of hydroxypropyl methylcellulose acetate succinate (hypromellose acetate succinate), cellulose acetate phthalate, hydroxypropyl methyl cellulose phthalate, polyvinyl acetate phthalate, sodium alginate, alginic acid, poly(methacrylic acid, methyl methacrylate) 1:1 and (Eudragit L100), poly(methacrylic acid, ethyl acrylate) 1:1 (Eudragit L30D-55).

A suitable enteric coating can be made from Eudragit™ polymers series (available from Rohm Pharma) which are polymeric lacquer substances based on acrylates and/or methacrylates. Suitable polymers which are slightly permeable to water, and exhibit a pH-dependent permeability include, but are not limited to, Eudragit™ S (poly(methacrylic acid, methyl methacrylate) 1:2); Eudragit L100™ (poly(methacrylic acid, methyl methacrylate) 1:1); Eudragit L30D™, (poly(methacrylic acid, ethyl acrylate) 1:1); and (Eudragit L100-55) (poly(methacrylic acid, ethyl acrylate) 1:1). Eudragit™ L is an anionic polymer synthesized from methacrylic acid and methacrylic acid methyl ester. It is insoluble in acids and pure water. It becomes soluble in neutral to weakly alkaline conditions. The permeability of Eudragit™ L is pH dependent. Above pH 5.0, the polymer becomes increasingly permeable. Mixtures of such polymers may also optionally be used.

The polymer coat will help to maintain the intra-capsule composition and pH and therefore the micro-environment of the capsule.

It is expected that when capsules will be dissolved and/or burst and/or disintegrate and/or degraded the micelles will be adsorbed to the GI tract mucosa according to their electrical charge and the charge of the mucosa (inflamed or non inflamed).

With regard to other types of tissues and routes of administration, under normal physiological conditions, the pH of plasma and tissues is maintained at values slightly above neutral pH, in a very narrow range of pH values from approximately 7.38 to 7.42. Some pathological conditions may lead to a systemic decrease in pH such as metabolic acidosis which can be caused by diabetic ketoacidosis, alcoholic ketoacidosis, ketoacidosis due to starvation, poisonings (e.g., methanol, ethylene glycol, salicylates, etc.), severe diarrhea, enzyme defect, and the like. All of these conditions can result in a decrease in systemic pH, although not below pH 7.0, even in severe cases. A similar decrease can be observed in respiratory acidosis that can be caused by decreased ventilation, whether acute or chronic.

In addition to disease conditions that result in a systemic decrease in pH, there are many diseases in humans that produce a localized decrease in pH. These conditions include a wide variety of infectious diseases, as well as many tumors which are related to hypermetabolic activity and/or hypoxic state, all of which are capable of inducing the phenomenon of a localized decrease in normal physiological pH. In localized infectious diseases, the pH can be as low as 4.5, whereas in tumor sites, the pH is 0.7 to 1.0 pH unit lower than normal physiological pH.

Without wishing to be limited in any way, it has been demonstrated herein that the beta-casein assemblies described herein, when formed in acid aqueous solutions and maintained at a low pH (below the protein pI), have a unique disk-like shape, which has never been previously demonstrated for a self-assembling protein system. This new form of assembly provides the unloaded carrier improved properties over other systems. Among these improved properties and without wishing to be limited by a single hypothesis, the assemblies have been shown to exhibit one or more of the below characteristics: insensitivity of the shape, size or aggregation number to changes in the temperature; stability to changes in pH, within a wide range of acid pH conditions; increased stability to damage or degradation upon storage, namely, longer shelf-life of the unloaded vehicles compared to beta-casein micelles at neutral pH.

According to some embodiments, the compositions according to the present invention have one or more therapeutic applications, including as a carrier for any type of therapeutic agent as described herein (in some embodiments with the provisos and limitations also as described herein). A non-limiting example of a use of the compositions according to the present invention is for delivery of one or more therapeutic agents to the GI tract for treatment of either local (e.g., inflammatory conditions) or systemic conditions. The present invention may optionally be used, in some embodiments, to treat any GI tract disease. Gastrointestinal diseases and disorders include, without being limited thereto, inflammatory, infectious, gastrointestinal motility disorders, gastroesophageal reflux disease (GERD), chronic intestinal pseudo-obstruction (or colonic pseudo-obstruction, disorders and conditions associated with constipation as well as other conditions known to gastroenterologs. More specifically, the gastrointestinal diseases and disorders include, without being limited thereto, inflammatory bowel disease (IBD) including ulcerative colitis, Crohn's disease, peptic ulcer disease including gastric ulceration and duodenal ulceration, ileitis, colitis, ileocolitis, ulcerative proctitis, irritable bowel syndrome, gastroenteritis, diverticulitis, diverticulosis, reflux, ulcer, gastritis, dyspepsia, nausea, abrasion to gastrointestinal tract, heart burn, hiatal hernia, gastrointestinal abscess, aralytic ileus and diarrhea, constipation associated with use of opiate pain killers, post-surgical constipation, and constipation associated with neuropathic disorders and combinations thereof.

The inflammatory condition may optionally comprise any inflammation of the mucosa, for example. The GI mucosa is optionally selected from one or more of intestinal mucosa, small bowel mucosa, large bowel mucosa or the mucosa in the rectum. The term "mucosa" as used herein denotes the moist tissue lining body cavities (such as alimentary canal, nose, lungs, vagina), secretes mucous and covered with epithelium; however for this embodiment, specific reference is made to the intestinal mucosa. Histologically, the intestinal mucosa is divided into three layers: epithelial lining, lamina propria (support), muscularis mucosa (smooth muscle layer). It is supported by the submucosa (a loose collagenous tissue contains blood vessels, lymphatics, & nerves) and the muscularis propria (smooth muscle inner circular layer, outer longitudinal layer).

The inflammatory disease or disorder of the GI mucosa is optionally and preferably associated with long term oxidative stress or short term oxidative stress. More preferably, the disease or disorder is selected from ulcerative colitis, Crohn's disease, gastric ulceration, duodenal ulceration, ileitis, colitis, ileocolitis, ulcerative proctitis, gastroenteritis, diverticulitis, diverticulosis, reflux, ulcer, gastritis, dyspepsia, nausea, abrasion to gastrointestinal tract.

The micelles may optionally be a carrier for a therapeutic agent effective in inhibiting inflammatory responses. The therapeutic agent is more preferably selected from steroids, salicylates, COX-2 inhibitors, anti-TNF-alpha drugs, antibiotics, immunosupressors, immunomodulators and antioxidants. Most preferably, the therapeutic agent is selected from Prednisone, Prednisolone, methylprednisolone, methylprednisolone succinate, Budesonide, derivatives of 5-aminosalicylic acid, Sulfsalazine, Mesalamine (5ASA), Olsalazine, Balsalazide, Metronidazole, Ciprofloxin, Probiotics, Cyclosporin A, Azathioprine, Methotrexate and 6-Mercaptopurine.

The micelles may optionally, additionally or alternatively, comprise one or more anti-oxidants, including but not limited to tocopherol, free radicals scavengers, SOD and SOD mimics, catalase or therapeutic reducing agents.

For these uses, optionally any of the compositions described herein may be applied, including without limitation compositions prepared at pH values below the pI of the beta-casein protein and compositions prepared at neutral pH values.

The solubility and stability of the drugs significantly increases upon mixing with the beta-casein assemblies of the present invention.

According to some embodiments of the present invention, the loaded beta-casein assemblies demonstrate increased solubility of poorly-soluble compounds and/or improved loading of therapeutic molecules into the beta-casein micelles. Typically the protein to drug molar ratio will be in the range of 1:1 to 1:5 but ratios up to 1:10 may be achieved (e.g., sodium clodronate).

One of skill in the art can easily calculate the amount of protein required to achieve the desired dosage using molar ratios of 1:1 up to 1:10 protein to drug.

By way of example, initial treatment with budesonide involves daily administration of 0.4-to 1.6 mg of budesonide followed by a maintenance treatment during which a daily dose of 0.2 to 0.4 mg of budesonide is recommended. Based on beta-casein to drug mole ratio of 1 to 2 about 12 to about 50 mg of beta-casein will be needed. A capsule containing 1 ml of 50 mg/ml of beta-casein dispersion will suffice to deliver the recommended daily dose of budesonide.

Furthermore, the loaded system may be at least as stable as the unloaded system, or even more stable, and may be stored for the same or longer time period compared to the empty vehicle at the low pH environment.

Some loaded systems according to the present invention remain nanometric in size, transparent or just slightly opalescent. Some guest molecules can further be stabilized in the form of larger complexes in the nano and/or micro range. This is reflected in increased turbidity. The suspensions of many guest molecules remain stable and do not precipitate over time, or as a function of temperature. Some guest molecules (e.g. MPS) may precipitate at low temperature in some formulations according to some embodiments of the present invention, but they are re-solubilized rapidly at room temperature, without loss of bioavailability or loss of activity of the active ingredient.

Materials and Methods

Cryo-TEM: Specimens were prepared in the controlled environment vitrification system (CEVS) (Bellare et al. *Electron Microsc. Technique*, 1988, 10;87-111) at 24° C. and 100% relative humidity to avoid loss of volatiles. First, the solutions were incubated in the CEVS at the desired temperature for 1 h. Then, a 7 µL drop of each solution was placed on a TEM copper grid covered with a perforated carbon film (Pelco International) and blotted with filter paper to form a thin liquid film of the sample (100-200 nm thick). The thinned sample was plunged into liquid ethane at its freezing temperature (−183° C.) to form a vitrified specimen and then transferred to liquid nitrogen (196° C.) for storage. The vitrified specimens were examined in a Philips CM120 transmission electron microscope operating at an accelerating voltage of 120 kV. We used an Oxford CT3500 (Oxford Instruments) cryoholder that maintained the specimens below −175° C. during sample transfer and observation. Images were recorded digitally on a cooled Gatan MultiScan 791 CCD camera using DigitalMicrograph 3.1 software (Gatan) in the low-dose imaging mode to minimize beam exposure and electron-beam radiation damage.

ITC: ITC measurements were performed with a VP-ITC calorimeter (MicroCal) at a temperature of 24° C. The reaction cell (V=1.43 mL) was filled with degassed solvent (lactic acid at pH 2.6, or phosphate buffer at pH 7.0). The injector-stirrer syringe (289 µL) was loaded with a β-casein micellar solution (20 mg/mL). The micellar solution was injected into the reaction cell in 28 steps of 10 µL aliquots each, and the heat flow was measured. During the titration, the stirring speed was 310 rpm. The duration of each injection was 20 s, and the equilibration time between consecutive injections was 3 min. Such an interval was sufficient to equilibrate the reaction cell after every injection. Each experiment was performed at least three times. Calorimetric data analysis was carried out using Origin 5.0 software (MicroCal).

Analytical Ultracentrifugation: Sedimentation equilibrium experiments were performed at 24° C. using a Beckman Optima XL-A (Palo Alto, Calif.) analytical centrifuge at 6000, 10000, and 12000 rpm for the low-pH solutions and at 4000, 6000, and 8000 rpm for the pH 7.0 solutions. Data were collected at 280 nm. The β-casein solutions were studied at concentrations ranging from 0.2 to 10.0 mg/mL at pH 2.6 and from 0.2 to 2 mg/mL at pH 7.0 and an ionic strength of 0.1. Past studies showed that the protein self-assembly is not affected by pressure and, therefore, it is not speed-dependent. The average apparent molecular weight of the micelles at the various protein concentrations was calculated following methods well known in the art (The partial specific volume vj of the solute was taken to be 0.742 cm3/g3, and a solution density F of 1.0044 g/cm3 was measured). At β-casein concentrations of 2 mg/mL and above under low pH conditions, the plot of the natural logarithm of the measured absorbance versus the square of the radius from the axis of rotation was not linear. To estimate Nagg, the limiting slope toward the outer edge of the sample cell was used to provide $d\ln(c)/dr^2$. The molecular weight calculated using this slope was divided by the monomer molecular weight calculated from the β-casein amino acid sequence (24000).

Small Angle X-ray Scattering (SAXS): The small angle x-ray scattering equipment consisted of a SAXSess camera (Anton-Paar, Graz, Austria) connected to an x-ray generator (Philips, PW 1730/10) operating at 40 kV and 50 mA with a sealed-tube Cu anode. A Gobel mirror was used to convert the divergent polychromatic x-ray beam into a focused line-shaped beam of Cu Kα radiation (λ=0.154 nm). The 2D scattering pattern was recorded by a PI-SCX fused fiber optic taper CCD camera from Princeton Instruments, which is a division of Roper Scientific, Inc. (Trenton, N.J., USA). The used CCD detector features a 2084×2084 array with 24×24 μm pixel size (chip size: 50×50 mm). The CCD was operated at −30° C. with 10° C. water-assisted cooling to reduce the thermally generated charge. Cosmic ray correction and background subtraction were performed on the 2D image before further data processing. The 2D image was integrated into the one-dimensional scattering function within a band of 10 mm. The measurement time was 30 min for each scattering curve (6 images of 5 minutes were taken to assist the cosmic ray correction).

Density Measurements. The specific gravity of the solvents and the protein solutions was measured by a density meter DMA 5000 from Anton-Paar at various temperatures. These measurements enabled an accuracy of six digits.

Determination of the Beta-Casein Assemblies Molecular Weights.

The molecular weight of the scattering aggregates were calculated according to Eq. 1:

$$M = \frac{d\Sigma(0)}{d\Omega}(N_A/c\Delta\rho_M^2) \quad (1)$$

where M is the molecular weight, $d\Sigma(0)/d\Omega$ (cm$^{-1}$) the forward scattering intensity at q=0, c (g/cm$^3$) the beta-casein concentration, $N_A$ the Avogadro number, and $\Delta\rho_M$ (cm/g) the scattering length difference per mass, given by:

$$\Delta\rho_M = \Delta\rho\bar{v} \quad (2)$$

The scattering length difference Δρ (cm$^{-2}$) was calculated using the known chemical composition of the protein and the solvent, and $\bar{v}$ (cm$^3$/g), the specific volume of the protein in the solution that was calculated via density measurement of the solvent and the solution. The micelle aggregation number was then calculated by dividing the molecular weight of the micelles determined with Eq. 1, by the molecular weight of a single protein molecule.

PDDF Determination.

For a particle of arbitrary shape with a scattering density difference of Δρ(r), the pair distance distribution function p(r) (PDDF) is given by:

$$p(r) = r^2 \Delta\rho^{-2}(r) \quad (3)$$

where $\Delta\rho^{-2}(r)$ is the convolution square of Δρ(r) averaged for all directions in space. The PDDF is related to the scattered intensity I(q) by a Fourier transformation, and it enables the determination of the overall shape and size of the scattering objects.

$$I(q) = 4\pi \int_0^\infty p(r) \frac{\sin(qr)}{qr} dr \quad (4)$$

where q is the magnitude of the scattering vector q, defined as $$q = \frac{4\pi}{\lambda} \sin\left(\frac{\theta}{2}\right) \quad (5)$$

λ is the wavelength of the incident radiation and θ is the angle between the scattered and incident beam. The function $$f(r) = p(r)/r \quad (6)$$

is useful to identify flat plate-like particles, although it has no direct physical meaning. For lamellae, this function starts with a linearly increasing part and becomes almost flat when r is equal to the thickness of the lamella. For flat particles with a finite base area, the outer part decreases linearly because of boundary losses. The thickness of the lamella can then be read from the transition point. Hence, in practice, the shape of the function $f(r)$ allows the recognition of lamellar particles and determination of their thickness.

Statistical Analysis: For each of the methods applied, a statistical analysis of the data was performed, based on at least three separate replicate experiments. The standard error of the ITC data was found to be no more than 5% for the CMC and MR values and no more than 3% for ΔHdemic. The standard error of the analytical ultracentrifugation data is 5%, and that of the Rg is 4%. The analysis supports the statistical significance and validity of the results.

EXAMPLE 1

Preparation of beta-casein assemblies: Weighted amounts of lyophilized bovine beta-casein are dissolved in low-pH solution (e.g. ~6% by weight of lactic acid solution or hydrochloride acid solution, ~pH 2.1), typically at concentrations ranging from 0.1 mg/mL up to at least 50 mg/ml, to the desired pH (2.3-2.8), below the pI. The pH can be adjusted to the desired values using appropriate buffers. Mixing is done at room temperature, and the solution is equilibrated at 4° C. for ~36 hr, allowing complete solubilization and formation of the protein assemblies. Thereafter, the solutions can be held at any temperature between 1 and 60° C.

Similarly, to prepare beta-casein micelles at neutral pH, weighted amounts of lyophilized protein were added to a buffer at neutral pH (e.g., HEPES buffer, or PBS), at concentration ranging from 0.1 mg/ml to ~50 mg/ml.

Complete solubilization of the protein is achieved within about 1 hr to about 36 hr, at temperatures ranging from 4° C.

to about 40° C. A transparent solution is obtained, containing unique nano-sized beta-casein assemblies. The protein solutions are filtered through a porous membrane of 0.45 micron pore size. The beta-casein concentration was determined by measuring the absorbance at 280 nm by an Ultrospec 2000 UV/Visible spectrophotometer (Pharmacia Biotech, England), using an extinction coefficient of 4.6 $_{(1\%)}$ mM$^{-1}$cm$^{-1}$. Other methods to determine protein concentration such as Lowry can also be used. The stock solution is diluted with an acidic solution having the same pH, to the final concentration required, typically between 0.1 mg/ml and 20 mg/ml. The ionic strength and Osmolarity can be adjusted by mixing the vehicles-containing solution with a salt-containing electrolyte (or without salt) solution, both having the same pH. The solution can be stored at 4° C., for at least several months, more specifically for at least 3 months preferably at least 6 months, depending on the storage medium pH, ionic strength, and osmolarity The novel low and neutral pH beta-casein assemblies of the present invention have been characterized by various techniques including: isothermal titration calorimetry (ITC), small-angle x-ray scattering (SAXS), analytical ultracentrifugation, density measurements and cryogenic-transmission electron microscopy (cryo-TEM).

EXAMPLE 2

Density measurements of beta-casein solutions: Density measurements of the beta-casein solutions at pH 2.6 as a function of temperature are summarized in Table 1. Density measurements were performed using a density meter DMA 5000 from Anton-Paar, reaching an accuracy of six digits.

TABLE 1

Density measurements of beta-casein solutions, as a function of temperature, measured at pH 2.6.

| | Data of 20 mg/ml β-casein pH 2.6, lactic acid solution | | | |
|---|---|---|---|---|
| T [° C.] | 4 | 16 | 25 | 40 |
| Solvent density [g/cm$^3$] | 1.005274 | 1.003948 | 1.001878 | 0.996814 |
| Solution density [g/cm$^3$] | 1.010410 | 1.008926 | 1.006764 | 1.001588 |

EXAMPLE 3 beta-casein charge distribution: The distribution of charges along the beta-casein backbone and the beta-casein protein total charge at acidic and neutral pHs were calculated. FIG. 1 shows the protein sequence and distribution of charges at the two pH regimes. At pH 6.7, most charges are concentrated at the N-terminus, while the long C-terminus is highly hydrophobic. A net charge of −13.28 was calculated at this pH, in good agreement with previous calculations at similar pH values. At a low pH of 2.6, the protein net charge is somewhat larger (+15.82 vs −13.28). The charge distribution, however, changes significantly. A cluster of negative charges is present in sequences 15-20. Sequences 25-50 contain a cluster of six positive charges and sequences 97-113 contain another cluster of six charges, while the domain in between does not have any charge. Additionally, a large number of positive charges are distributed along the hydrophobic C-terminus. Thus, overall, this picture indicates that in an acidic environment, the protein loses the distinct separation between hydrophilic and hydrophobic domains.

EXAMPLE 4

Characterization of the beta-casein micelles by cryo-TEM: The structural characteristics of the micelles in the two pH environments were studied by cryo-TEM and SAXS (Small Angle X-ray Scattering). Cryo-TEM was used to determine the shape of the micelles and to estimate their dimensions between 4 and 40° C. This information was further used to accurately calculate the micelles' dimensions from the SAXS data, and to study how the size and shape are affected by temperature. SAXS measurements also provided the critical micelle concentration (CMC) and the micelle aggregation numbers as a function of temperature. Experiments were performed in the concentration range of 0.1-40 mg/mL protein, at low pH (between 2.1 and 2.6) in dilute lactic acid solution (6 wt %) or HCl and in aqueous solutions at pH 6.7 in the presence of 0.05M NaCl.

Figure 2:
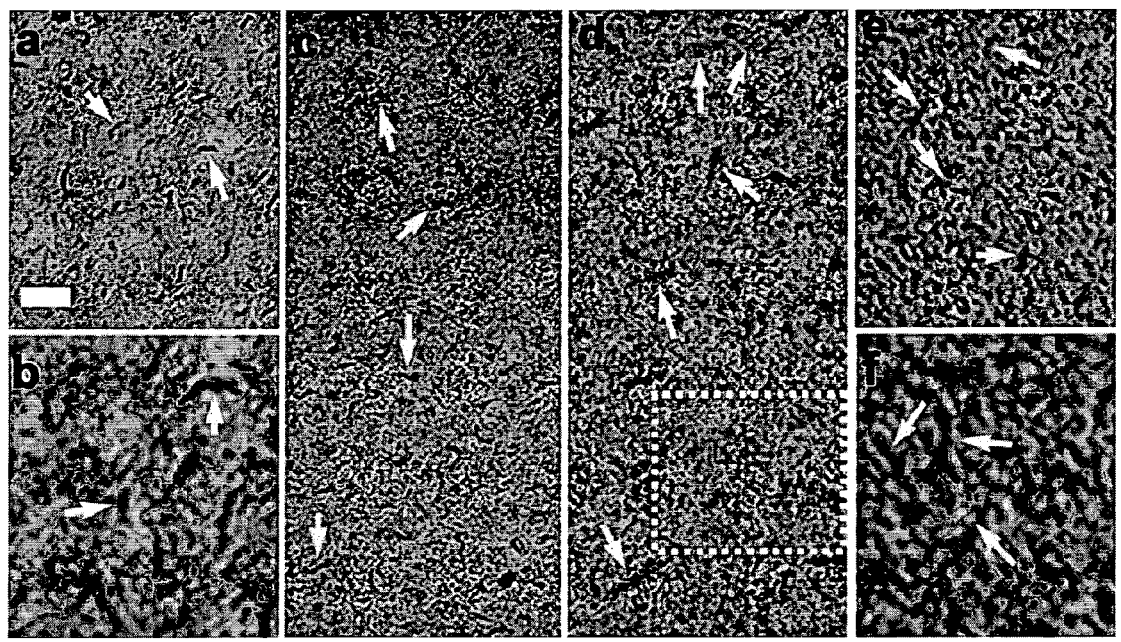
FIG. 2: Cryo-TEM images of 2 wt % β-casein micelles in lactic acid solution (pH 2.6): (panels a and b) 40° C., (panels c and d) 25° C., (panels e and f) 4° C. Panels a, c and e show low magnification regions populated with the protein micelles. Higher magnifications of these structures are given in panels b, d and f. All images show flat disc-like (plate-like) micelles. Due to the relatively low contrast of the thin micelles they are best seen when their flat surfaces are positioned parallel to the electron beam. In very thin specimens (e.g., image d) less structures and solvent (per unit volume) contribute to the 2-dimensional image, thus the micelles look more spaced, and additionally, micelles oriented with their flat surface perpendicular to the electron beam are also resolved (see, for example, the upper part of panel c, and the micelles enclosed in the dashed square in panel d). Arrows in the images point to few disc micelles, showing they have similar thickness and length under all the temperatures studied. Bar equals 50 nm (a, c and e) and 20 nm (b, d and f).

In the lactic acid solution (pH 2.6), flat disk-like micelles formed within the complete temperature range studied (4-40° C.), as shown in the cryo-TEM images presented in FIG. 2. From the 2-D projection of the micelles in the vitrified samples, the micelles are estimated to be 3-4 nm thick and to have elongated surfaces 20-25 nm in length. Micelles of similar shape and dimensions also form in HCl at the same pH at room temperature. This suggests that under the conditions studied, the nature of the solvent's counterion has little, if any, effect on the size, shape, and dimensions of the β-casein containing micelles. Overall, the cryo-TEM experiments show that at low pH, β-casein self-organizes into a homogeneous population of flat, disk-like micelles, whose shape and dimensions appear to be independent of the solvent counterion or the solution temperature.

The self-assembly behavior of the solution of 20 mg/mL β-casein at pH 6.7 and 0.05M NaCl was studied as a function of temperature. Flat micelles were observed at 4° C. and 10° C., but their contrast is relatively low, and consequently, their morphology is somewhat indistinct. At 16, 25, and 40° C., oblate micelles were detected. Relatively spheroidal micelles were found at the high temperature of 60° C.

EXAMPLE 5

Figure 3A:
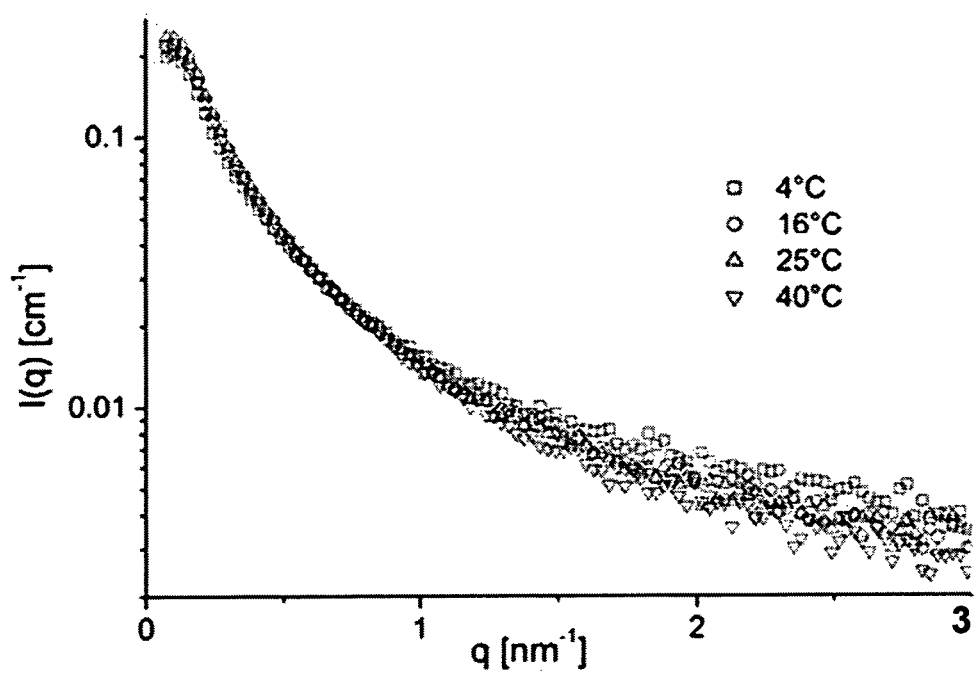
FIG. 3: (a) SAXS curves of 2 wt % β-casein solution at pH 2.6, at different temperatures. For better visibility, only each fifth experimental point of the scattering curves is shown. (b) Pair Distance Distribution Function (PDDF) obtained from the scattering curves by Indirect Fourier Transform (IFT). The area, which is proportional to the aggregation number, does not change significantly. The aggregation number was found to be similar at all temperatures. (c) Normalized PDDF deviates in shape from an homogenous sphere. rmax is the value of r where the PDDF has its maximum. (panel d) The function $f(r)$ indicates a plate-like particle shape with particle thickness of approximately 3.5 nm.
Figure 3B:
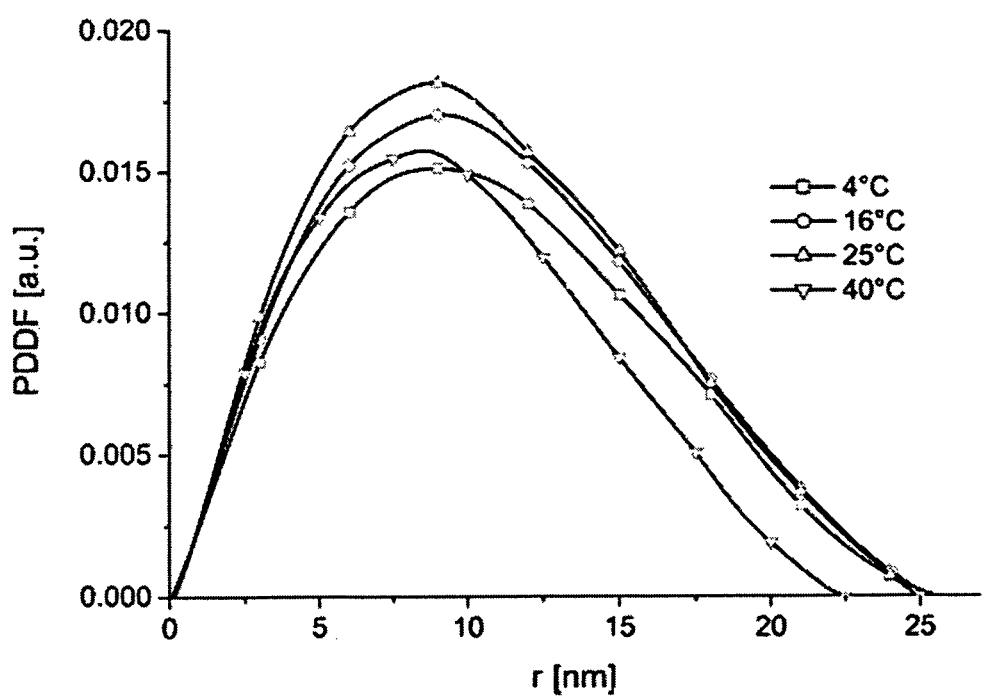
Figure 3C:
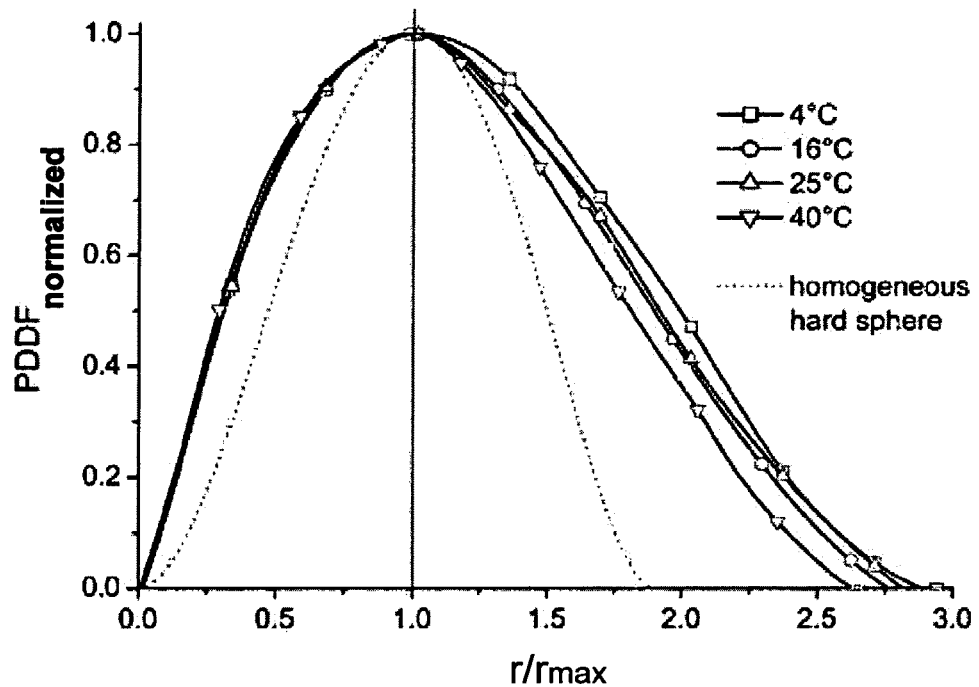
Figure 3D:
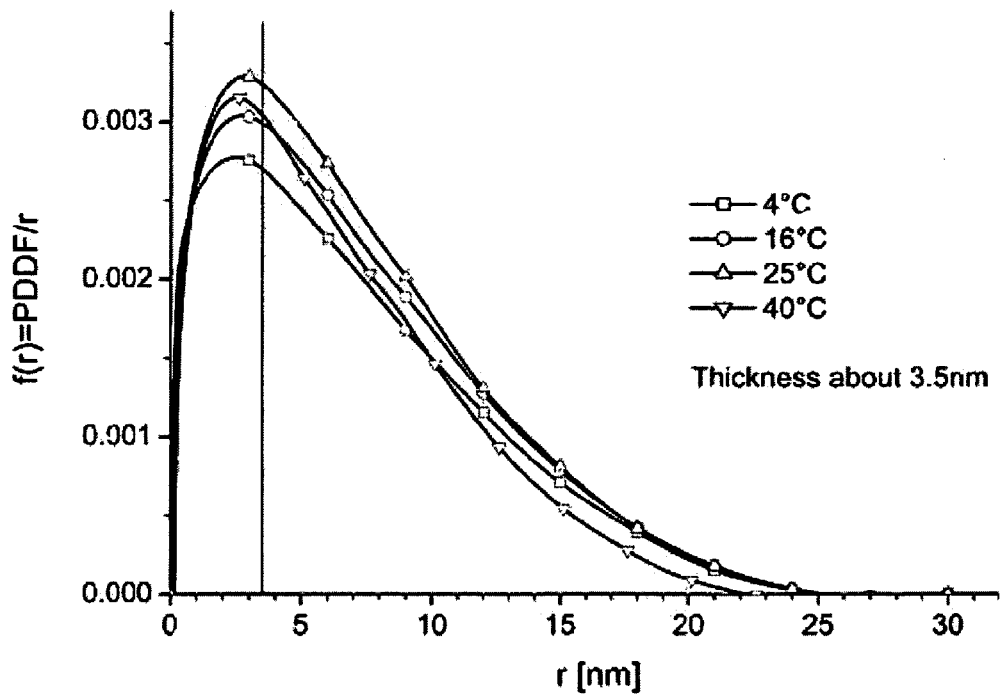

Characterization of the beta-casein micelles by SAXS: SAXS measurements were used to determine the shape and dimensions of the micelles at low pH more precisely, and to evaluate the micelle molecular weight (i.e., the aggregation number). The scattering curves of 20 mg/mL β-casein in lactic acid solution (pH 2.6, IS 0.0022) at different temperatures are shown in FIG. 3a. Interestingly, very little change in the scattering curves is observed in the complete range of temperatures studied (between 4 and 40° C.), as we also found by cryo-TEM (FIG. 2). Consequently, the calculated Pair Distance Distribution Functions (PDDF), are also similar (FIG. 3b). The maximum micelle dimension is approximately 25 nm at all temperatures. The area under the PDDF curve, which is proportional to the weight of one particle, is almost constant. To calculate the aggregation number, the density of the solvent and the solution was measured at various temperatures (Table 2). The aggregation number was found to vary only slightly (between 8 and 11) as the temperature was raised from 4 to 40° C. (Table 2). These differences are not significant, and they indicate that the micelle aggregation number remains practically constant within this wide range of temperatures, as was also indicated by the constant scattering profiles shown in FIG. 3a,b.

The shape of the PDDF gives information on the shape of the assemblies. The experimental PDDFs were compared with a theoretical PDDF of a homogeneous sphere, and all functions were normalized to a value of 1 at the x- and y-axes at the PDDF maximum (FIG. 3 panel c). It can be clearly seen that the micelles have a very similar shape at different temperatures. However, the particles' shape deviates strongly from the shape of a sphere. In fact, the curve shape is characteristic of scattering from flat, plate-like particles, as indeed was indicated by the cryo-TEM data (FIG. 2). As expected for flat particles, the function (r) (FIG. 3d) displays a peak after which it decreases almost linearly to the maximum dimension. From the transition point, which is marked with a line in FIG. 3d, the thickness of the particles was found to be close to 3.5 nm at all temperatures.

Figure 4A:
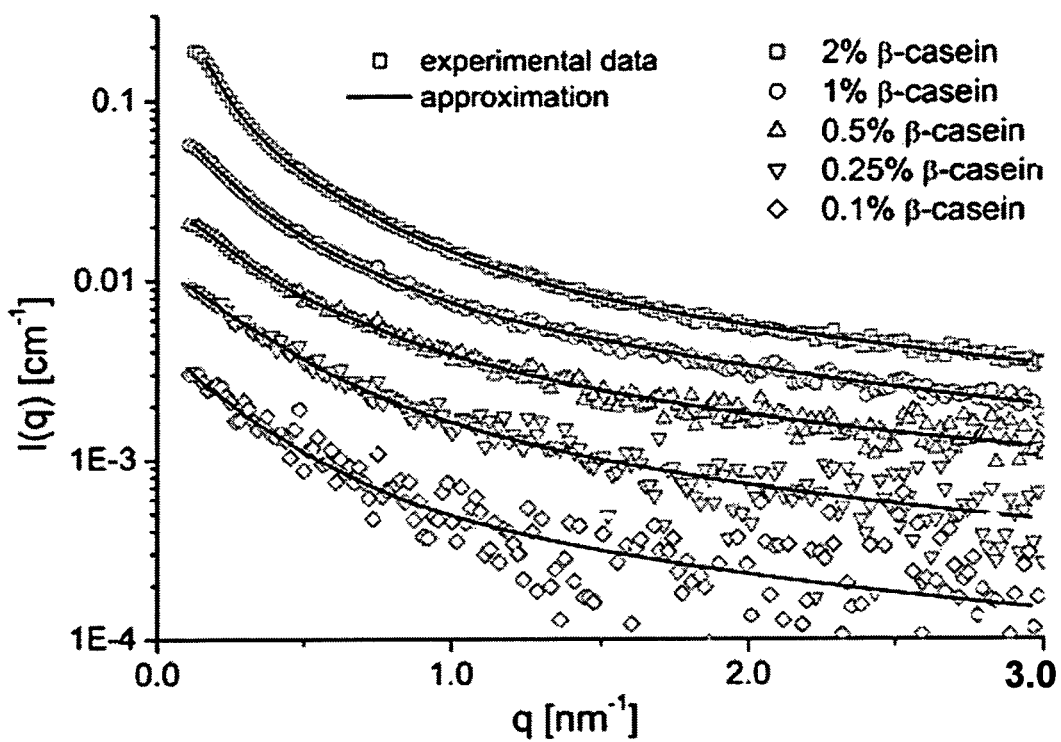
Figure 4B:
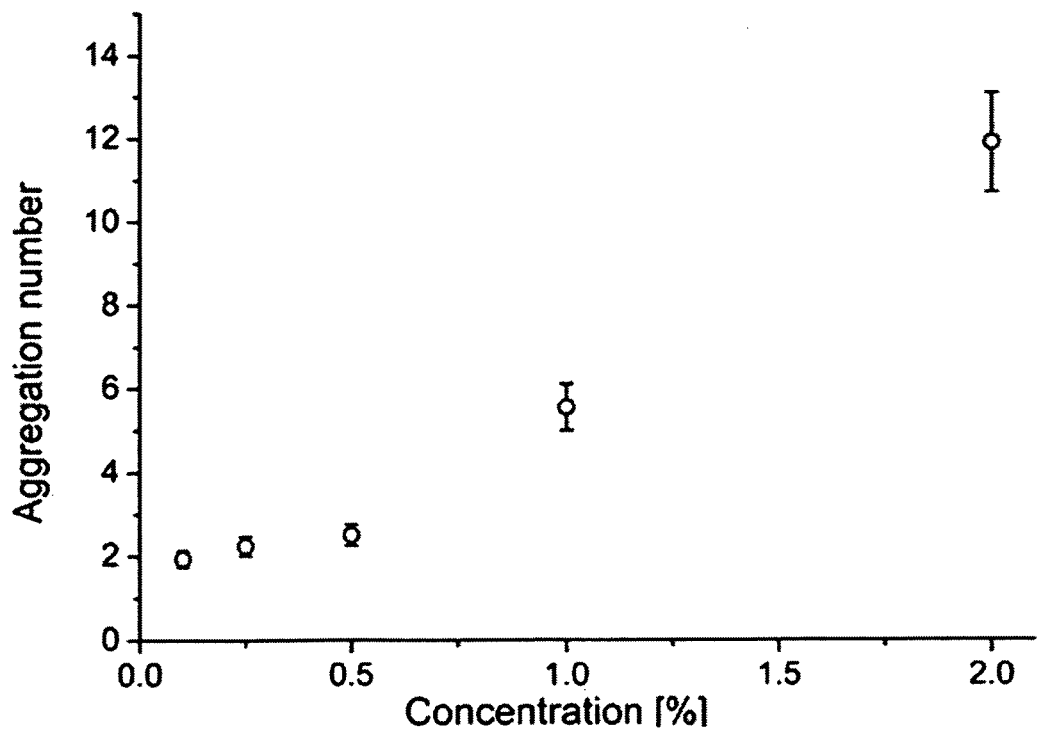

To determine the CMC and to investigate how the concentration affects the aggregation number, a series of dilutions, from 2.0 to 0.1 wt %, was prepared. The scattering curves were measured at 4° C. and were put on an absolute scale. The curves after subtraction of the solvent data are shown in FIG. 4a. As expected, the intensity of the scattering decreases when the concentration is decreased. But, in addition, there is also a change in the shape of the scattering curve. The upturn at low scattering angles is less pronounced at low concentrations, which indicates the presence of smaller particles. A detailed data evaluation described in the Experimental Procedures leads to the aggregation numbers shown in FIG. 4b. It is seen that above 0.5 wt %, Nagg strongly increases with the concentration, and at concentrations of 0.5 wt % and below, Nagg stays basically constant at a value of approximately 2. From this graph, the CMC of β-casein is estimated to be around 0.5 wt % at 4° C. An equivalent experiment was performed at 25° C. in which monomers were detected at the limit of dilution (0.1 wt %), dimers at 0.25 wt %, and a notable increase into higher oligomers at higher concentrations, suggesting that the CMC at 25° C. is in the range of 0.1-0.25 wt %. The decrease in the CMC (from 0.5 to 0.1-0.25 wt %) upon raising the temperature from 4 to 25° C. is also reasonable and may be explained by larger hydrophobic interactions at 25° C. than at 4° C., which drive the aggregation to occur at lower concentrations.

Figure 5A:
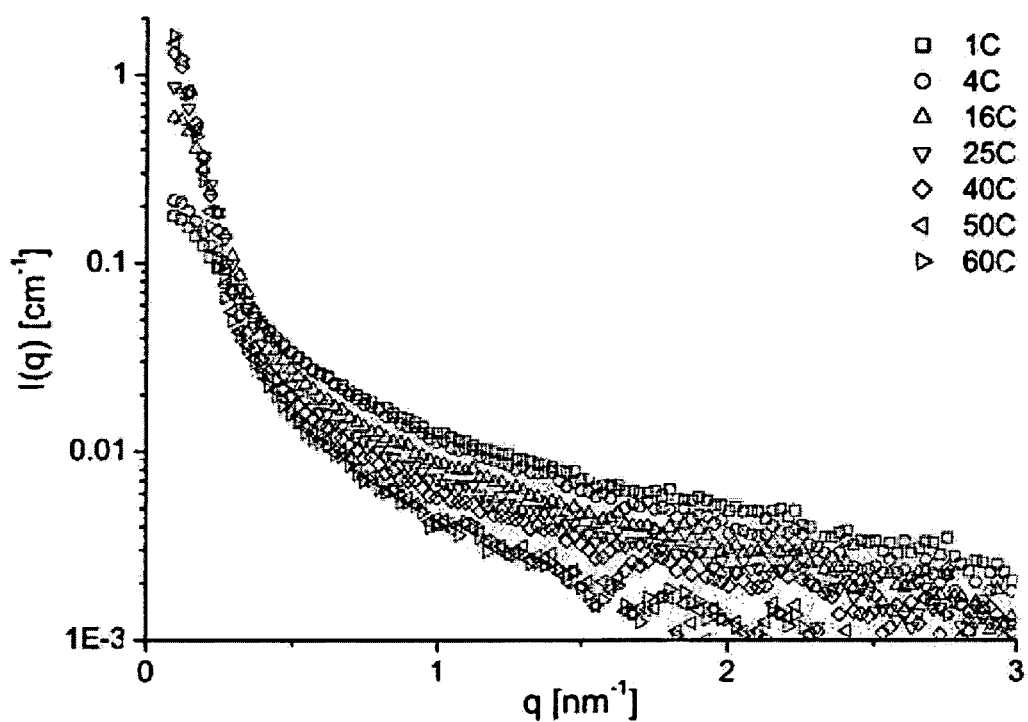
FIG. 5: (a) SAXS curves of a 2.0 wt % β-casein solution (pH 6.7) containing 0.05 M NaCl, at different temperatures. For better visibility, only each fifth experimental point of the scattering curves is shown. (b) The aggregation numbers determined from the scattering curves shown in panel a. The aggregation numbers increase with temperature. (c) PDDF obtained from the scattering curves by IFT. The area, which is proportional to the aggregation number, increases with temperature. (d) Normalized PDDF to show the deviation in shape from homogeneous monodispersed spheres.
Figure 5B:
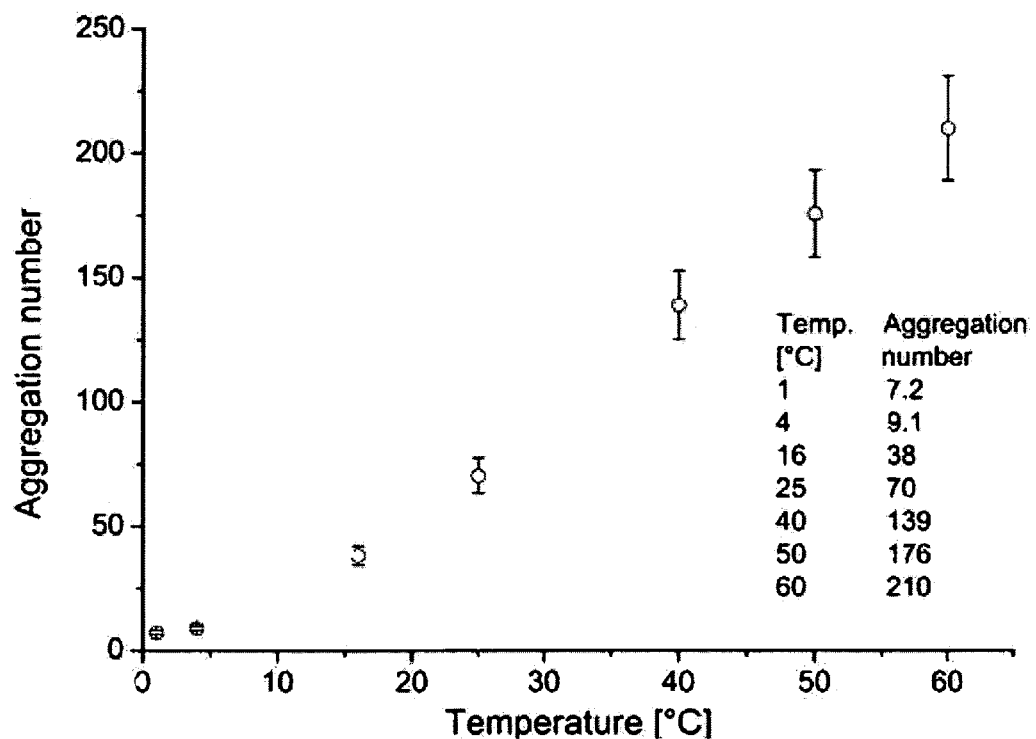
Figure 5C:
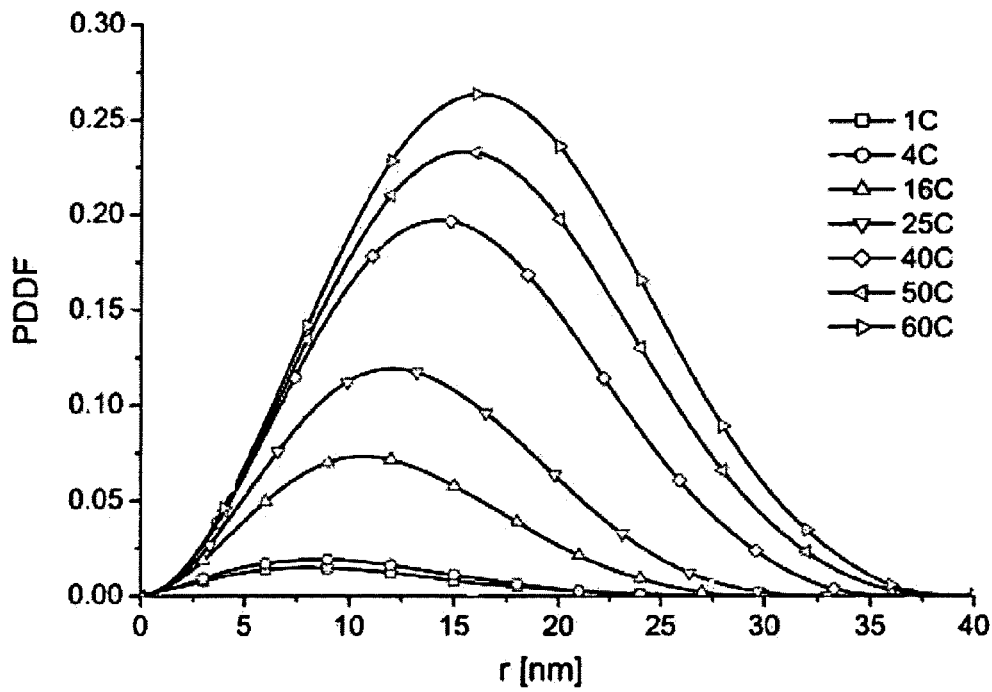
Figure 5D:
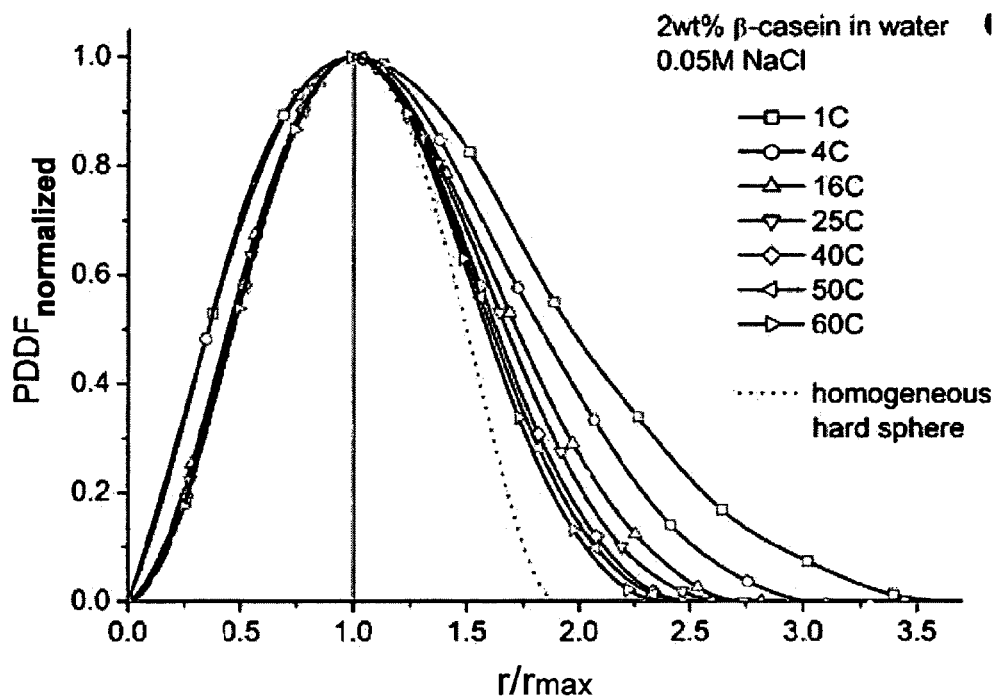

The β-casein micelles (20 mg/mL protein solutions) were further characterized at pH 6.7 in the presence of 0.05M NaCl at various temperatures between 1 and 60° C. (FIG. 5a). It is seen that the forward scattering intensity increases significantly in the low q regime but becomes smaller at high q values, as the temperature is increased. The aggregation numbers calculated from these data are shown in FIG. 5b. We find that the aggregation number increases from 7 to 210 as the temperature is raised from 1 to 60° C. As a result of the changes in the micelle dimensions, the area of the PDDF increases as well (FIG. 5c). The maximum dimension, which can be read from the point where PDDF reaches zero, grows from approximately from 25 to 40 nm. The shape of the micelles also changes upon heating. At low temperatures (4° C.), micelles exhibited a plate-like shape, similar to those existing at low pH. Interestingly, the deviation from the PDDF of a sphere is similar to that found at pH 2.6. However, the scattering data indicate that as the temperature is increased to 16° C. and above, the assemblies become more spheroidal in shape, which fits well with the formation of oblate and, at higher temperatures, more spherical micelles. As the temperature is raised further, the normalized PDDF curves show an almost perfect overlap with the theoretical curve of the sphere (FIG. 5d). No further growth was observed above 50° C.

TABLE 2

Characteristic properties of the micellar solutions and the micelles determined by SAXS as a function of temperature at acidic pH environment.

| pH  | T, (° C.) | CMC (wt %) | $N_{agg}$ | Micelle Shape | Micelle Dimensions |
|-----|-----------|------------|-----------|---------------|--------------------|
| 2.6 | 4         | 0.5        | 8         | disc          | Constant           |
|     | 16        | ND         | 10        | disc          |                    |
|     | 25        | 0.1-0.2    | 11        | disc          |                    |
|     |           | 0.19*      | 6*        |               |                    |
|     | 40        | ND         | 9         | disc          |                    |

ND - not determined;
*the CMC was found by isothermal titration calorimetry (ITC).

EXAMPLE 6

Figure 6:
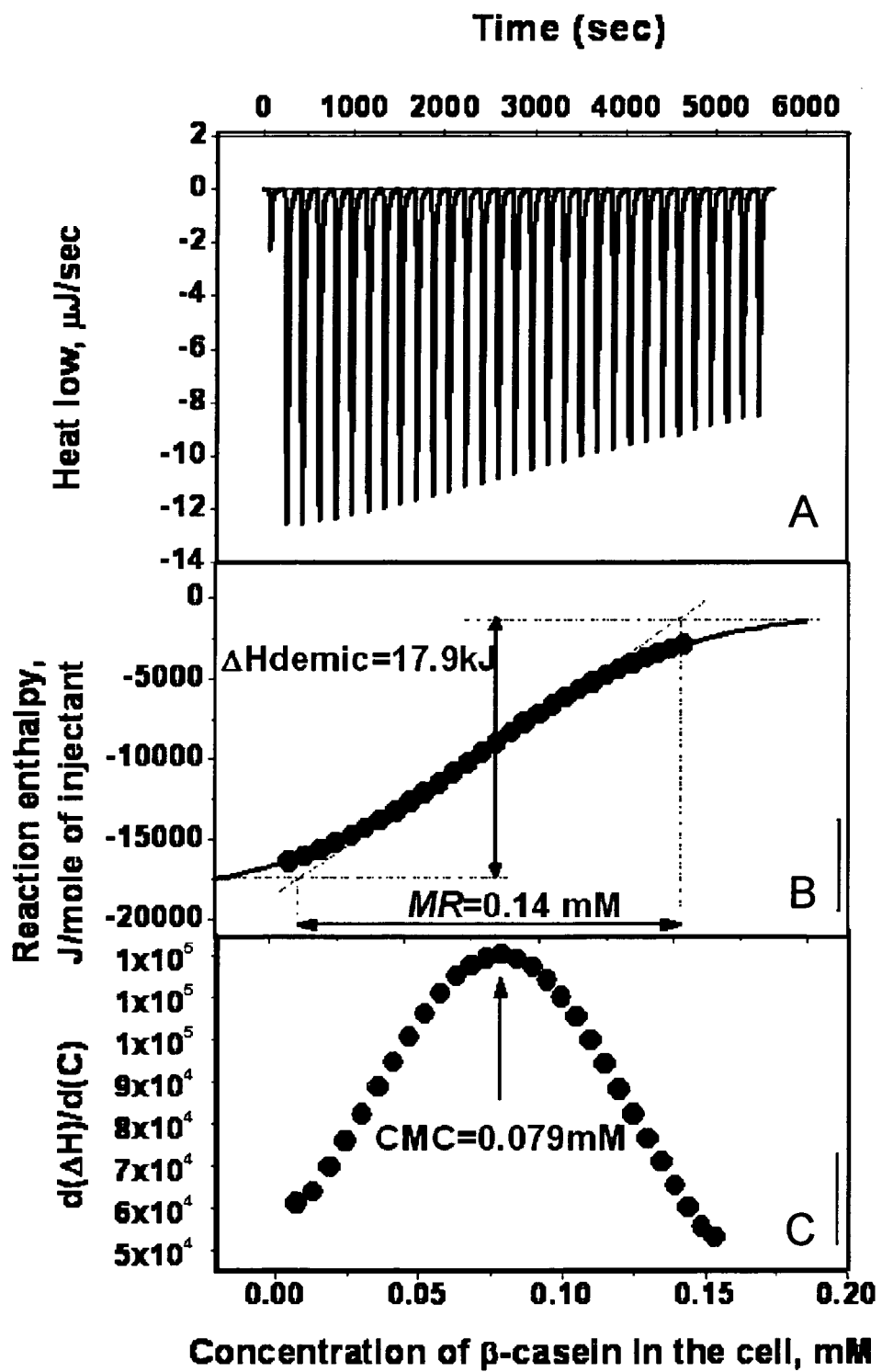
FIG. 6: Titration of micellar (20 mg/ml) β-casein solution in diluted lactic acid (pH 2.6) at very low ionic strength (0.002) into lactic acid solution, having the same pH and ionic strength, at 24° C.: (A) calorimetric traces, (B) reaction enthalpy vs. β-casein concentration in the cell, (C) first derivative of curve B calculated from the interpolated values.

Characterization of the beta-casein micelles by ITC: β-casein micellar solution was titrated into lactic acid buffer (pH 2.6) placed in the ITC cell, and the heat flow was measured as a function of time (FIG. 6A). Three factors contribute to the exothermic enthalpy changes observed at the initial injections: micelle dilution, demicellization, and dilution of individual β-casein molecules. The enthalpy changes decrease in magnitude as more protein is added and the concentration in the ITC cell increases. Eventually, the concentration in the cell exceeds the CMC and only micelle dilution contributes to the heat flow. In FIG. 6B the heat of the reaction, obtained by integrating the peaks of the individual injections given in FIG. 6A, is plotted against the β-casein concentration in the cell. A slow increase in the reaction enthalpy was observed, resulting in micellixation relative cooperativity (MR) of 0.14 mM (FIG. 6b), which is more than twice than the value found at pH 7.0 and IS of 0.1. FIG. 6B also presents the heat of demicellization, ΔHdemic, which equals the enthalpy difference between the two asymptotes of the sigmoid fit of the experimental data (obtained by using the Origin software). It is shown that at 24° C. ΔHdemic is ~−17.9 kJ/mol, relatively small compared with the −40.53 kJ/mol found at pH 7.0 and IS of 0.1. The CMC, obtained from the β-casein concentration at which the first derivative of the reaction heat displays a maximum, was determined to be 1.89 mg/mL (FIG. 6C) at pH 2.6. This value is approximately twice the CMC found at pH 7 and ionic strength 0.1. The small ΔHdemic, the high CMC, and the large MR indicate that the driving forces for micellization under acidic conditions are reduced compared with those at physiological pH and high IS.

EXAMPLE 7

Figure 7:
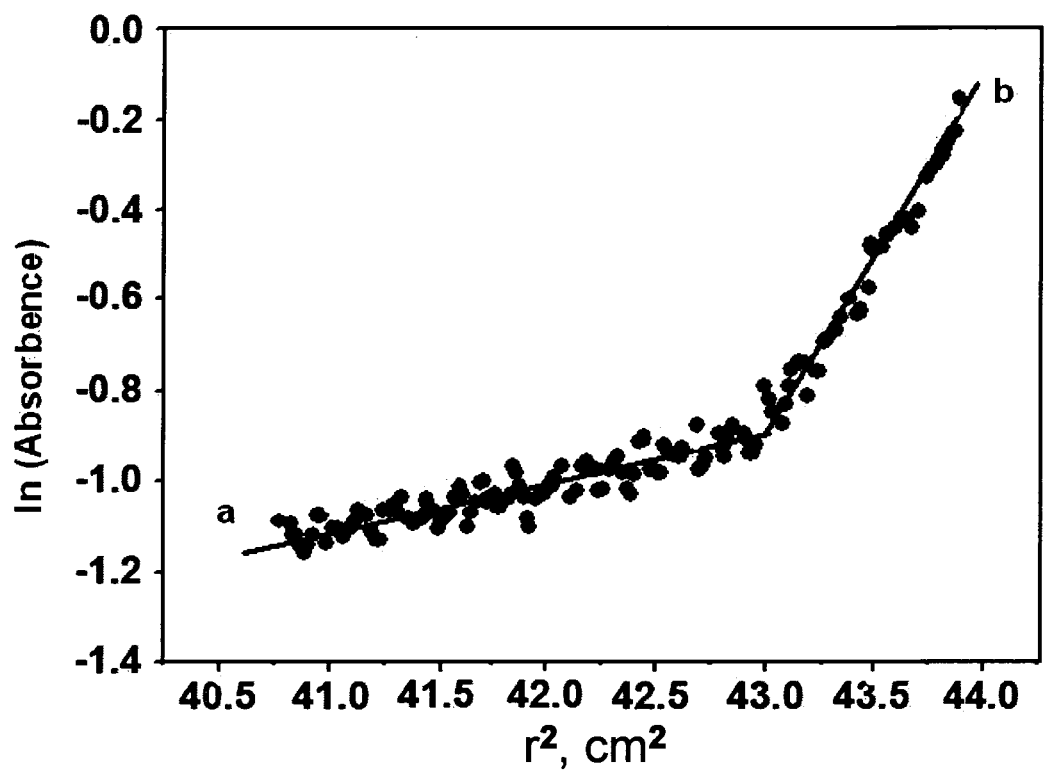
FIG. 7: Determination of β-casein aggregation number from the ultracentrifugation data at pH 2.6, protein concentration 5 mg/ml, ionic strength (IS) 0.002.

Characterization of the beta-casein micelles by Sedimentation Equilibrium: To determine the aggregation number of the micelles at pH 2.6, analytical ultracentrifugation experiments were conducted at various protein concentrations and at pH 7.0 and IS of 0.002. Sample data are plotted in FIG. 7, showing data with the protein concentration at 5 mg/ml, and ionic strength (IS) of 0.002. At concentrations lower than the CMC, determined by ITC to be 1.89 mg/mL (0.079 mM), a straight line was obtained. The aggregation numbers calculated from the slope of this line confirmed that the protein is monomeric at these concentrations. At concentrations higher than the CMC, two regions could be defined, indicating the presence of two protein populations: monomers at relatively short radii (i.e., in FIG. 7 at r<6.5 or r2<43) and assemblies at large radii. The micelles at pH 2.6 are characterized by a small aggregation number of 3 around the CMC and 6 at higher concentrations. In contrast, Nagg of 20 was measured at pH 7.0 and ionic strength 0.1. Thus, compared with assembly at neutral pH, assembly at low pH is characterized by two special features: the micelles are flat and disk-like in shape, and they have a low molecular weight.

EXAMPLE 8

Loading of guest low molecular weight molecules of different physico chemical properties into the β-casein assemblies: Calculated amounts of the guest molecules (usually a low molecular weight drug) were dissolved in ethanol. The dissolved guest molecule is then slowly titrated (2 microliter drops) into the vial containing the β-casein micelles. The solution is then strongly stirred, vortexed or sonicated for ~30 min depending on the type of encapsulated molecule, the overall concentration of the β-casein micelles and the molecule to be encapsulated, temperature, pH and ionic strength. Titration is continued until reaching the required drug-to-protein concentration. β-casein protein concentration after mixing ranges from 0.1% to 4%. Typical drug-to-β-casein protein concentrations at the final mixture ranges from 0.5:1 up to 10:1 at both acidic and neutral pH. The ethanol content might be up to 10% but is typically not more than 5%. The mixing, either by strong stirring, vortexing or sonication is usually done at room temperature for 30 minutes, or with solutions warmed to 40° C. Usually after an hour the turbidity is measured for the first time. The solubility and stability of the drugs significantly increases upon mixing with the β-casein.

The guest molecules can be varied in their physicochemical properties to include molecules which are highly hydrophobic and immiscible in water (the steroidal drug budesonide and Celecoxib), amphiphilic (the steroidal prodrug methylprednisolone hemisuccinate sodium salt (MPS)) and soluble in water in a pH dependent manner, or polar (ionic and nonionic) water soluble (e.g Sodium clodronate). Physical properties of these molecules are summarized in Table 3.

TABLE 3

The physical properties of budesonide, Celecoxib, MPS and Sodium clodronate.

| Properties | Budesonide | Celecoxib | MPS | Sodium clodronate |
|---|---|---|---|---|
| Molecular Weight | 430.53 | 381.37 | 474.54 | 244.9 |
| $pK_a$ | 12.85 ± 0.10 | −6.12 ± 0.50 (most basic, 25° C.) 9.68 ± 0.10 (most acidic, 25° C.) | 4.29 ± 0.17 | 7.37, 8.07 |
| Polar surface area $A^2$ | 93.1 | 86.4 | 138.2 | 134.7 |
| Total area $A^2$ | 638.1 | 484.1 | 380.54 | 226.9 |
| Non-polar Area $A^2$ | 545 | 397.7 | 242.34 | 92.2 |
| Non-polar/polar | 5.85 | 4.60 | 1.75 | 0.68 |
| ASA_$H^e$ | 441.2 | 370.5 | 404.40 | 62 |
| ASA_$P^f$ | 94.9 | 240 | 190.50 | 258.9 |
| ASA_H/ASA_P | 4.65 | 1.54 | 2.12 | 4.18 |
| Intrinsic Molar Solubility | 3.5E−5 mol/L | 1.3E−6 mol/L | 1.7E−5 mol/L | 30.5 mM |
| Molar Solubility [pH] | 3.5E−5 mol/L [1] to [10] | 1.3E−6 mol/L [1] to [8] | 1.7E−5 [1], [2] 1.8E−5 [3] 2.6E−5 [4] 1.1E−4 [5] 8.9E−4 [6] 8.1E−3 [7] | |
| logP | 3.142 | 4.213 | 2.688 | −0.85 |
| logD [pH] | 3.14 [1] to [10] | 4.21 [1] to [7] | 2.69 [1] [2] 2.67 [3] 2.51 [4] 1.9 [5] 0.98 [6] 0.02 [7] | −5.22 [4] −5.38 [5] −5.4 [6] −5.55 [7] −6.33 [8] −7.9 [9] |
| Charge [pH] | 0 [4-9] | 0 [4] 0 [5] 0 [6] 0 [7] −0.01 [8] −0.06 [9] | −0.69 [4] −0.96 [5] −1 [6] −1 [7] −1 [8] −1 [9] | −2 [4] −2 [5] −2.05 [6] −2.38 [7] −3.27 [8] −3.87 [9] |

EXAMPLE 9

Representative results with Celecoxib in acidic and neutral pH: Celecoxib is a non-steroidal anti-inflammatory drug (NSAID) used in the treatment of osteoarthritis, rheumatoid arthritis, acute pain, painful menstruation and menstrual symptoms, and to reduce numbers of colon and rectum polyps in patients with familial adenomatous polyposis.

Celecoxib is licensed for use in osteoarthritis, rheumatoid arthritis, acute pain, painful menstruation and menstrual symptoms, and to reduce the number of colon and rectal polyps in patients with familial adenomatous polyposis. It was originally intended to relieve pain while minimizing the gastrointestinal adverse effects usually seen with conventional NSAIDs. In practice, its primary indication is in patients who need regular and long term pain relief: there is probably no advantage to using celecoxib for short term or acute pain relief over conventional NSAIDs. In addition, the pain relief offered by celecoxib is similar to that offered by paracetamol. Celecoxib is another non-limiting example of a non-chemotherapeutic agent according to the present invention.

Figure 8A:
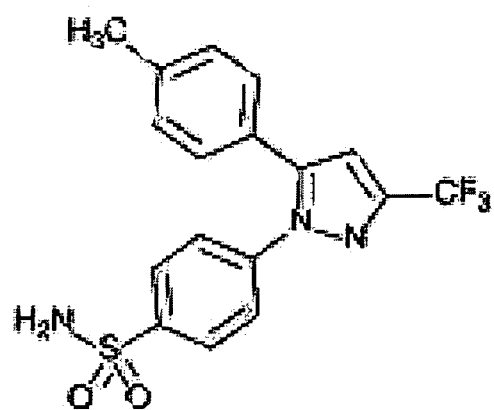
FIG. 8: (A) The chemical structure of celecoxib. (B) Photographs of celecoxib in lactic acid (a-c) and in 2% beta-casein, at increasing drug content; 0.5:1 (a1), 1:1 (b1) and 2:1 (c1)
FIG. 8C shows a photograph of celecoxib in hepes buffer with 2% of beta-casein with a drug:beta-casein ratio of 4:1 (left vial) and a total concentration of celecoxib of 24 mg/ml (right vial—celecoxib only).
Figure 8B:
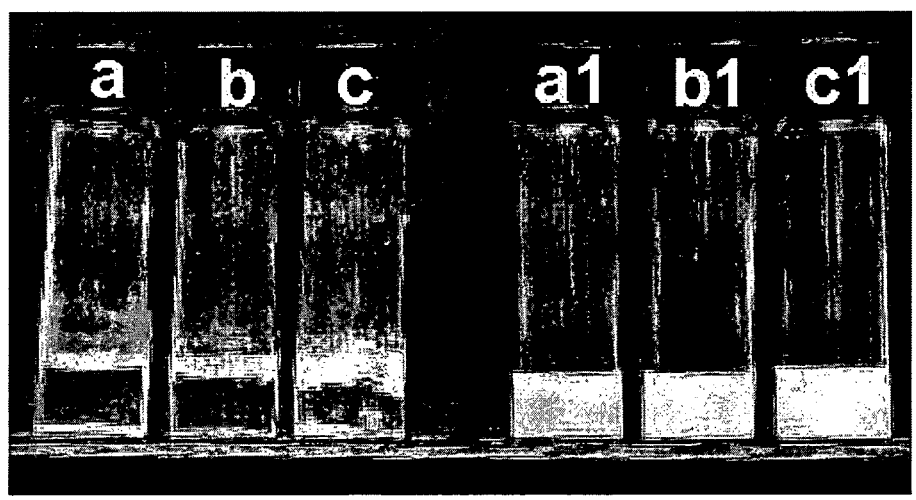
Figure 8C:

FIG. 8A shows the chemical structure of Celecoxib, while FIG. 8B shows photographs of celecoxib in lactic acid (a-c) and in 2% beta-casein, at increasing drug content. The suspension containing the loaded vehicles is stable over long times.

Figure 9:
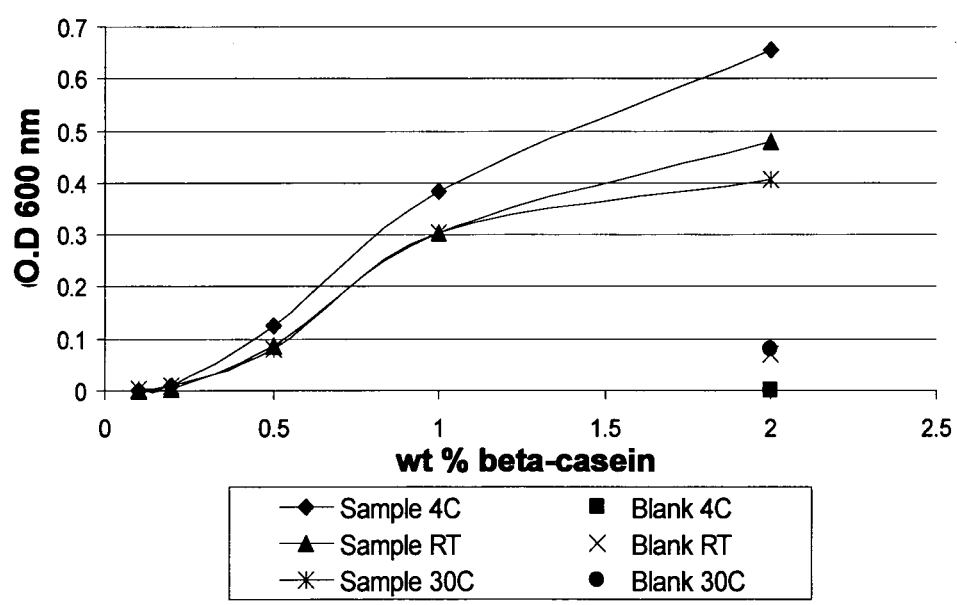
FIG. 9: Turbidity as a function of β-casein concentration and temperature for 1:1 β-casein to Celecoxib ratio solution in lactic acid solution, pH 2.6.

FIG. 9 shows the variation of the turbidity of beta-casein/Celecoxib solutions (lactic acid solution, pH 2.6). At 4° C. the complexes reversibly precipitate, and at room temperature they are rapidly re-dispersed in solution. The blank solution is transparent due to the immiscibility of the drug in the buffer. The protein solution is also transparent because it includes only small assemblies of up to ~20 nm in diameter.

Figure 10:
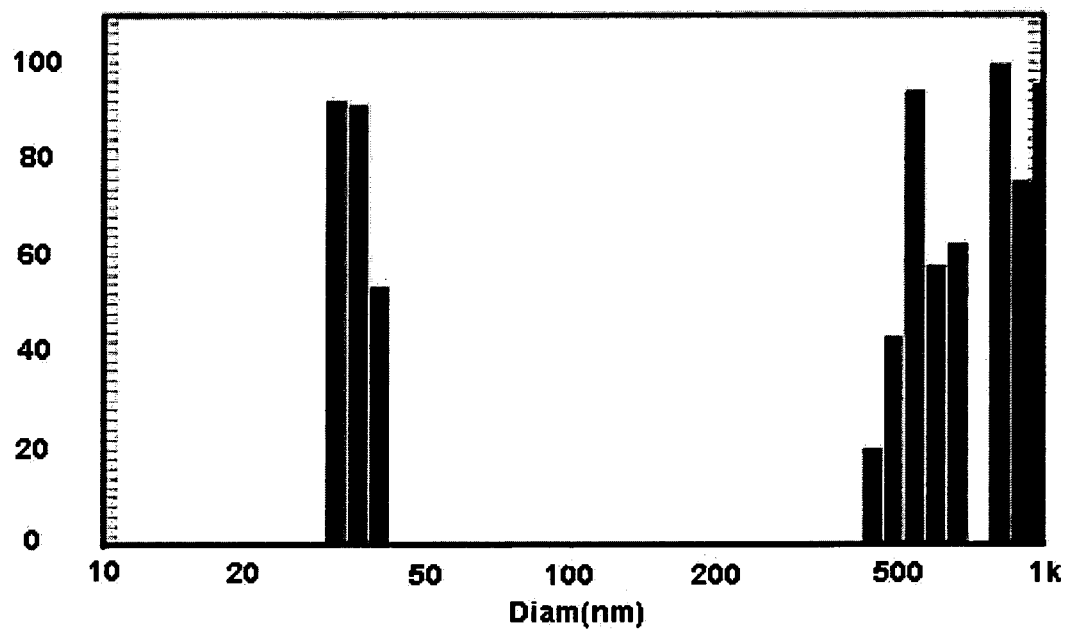
FIG. 10: Dynamic light scattering (DLS) data of celecoxib/protein complexes in lactic acid solution. 1 wt % beta-casein, 1:1 drug-protein molar ratio.

FIG. 10 shows, in a dynamic light scattering experiment, two distinct populations were observed: swollen micelles with characteristic diameter of 30-40 nm, and large complexes of 0.5 micron and up. The population of small assemblies is directly observed by cryo-TEM (as detailed below); the assemblies that are in the micrometer range are visible by light microscopy at Nomarski optics.

Figure 11:
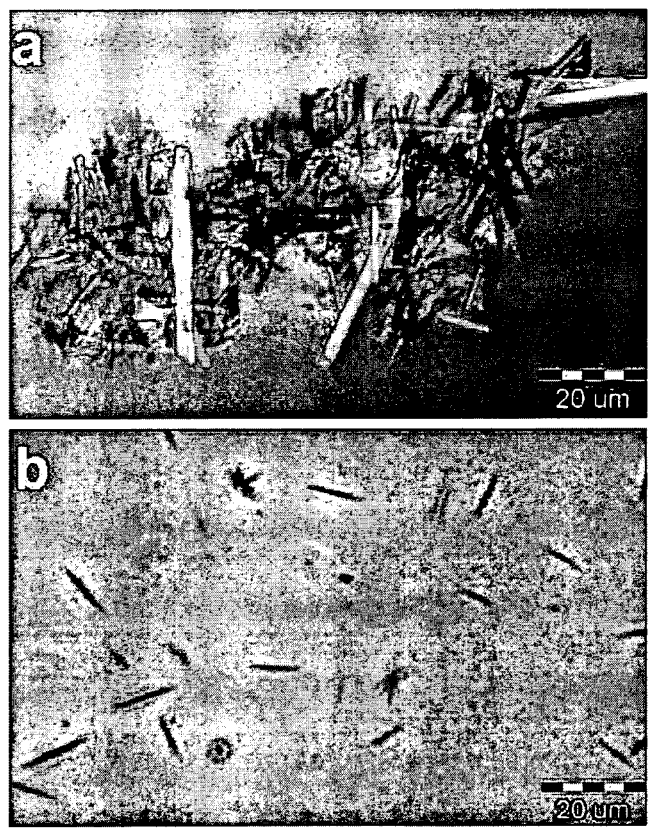
FIG. 11: light microscopy images at pH 2.6 showing: (a) large crystals of Celecoxib in lactic acid buffer. (b) celecoxib in the same solution and pH, in 1 wt % beta-casein at protein:drug molar ratio of 1:0.5. The same amount of drug is present in a and b.

FIG. 11 features light microscopy images at pH 2.6 showing: (a) large crystals of Celecoxib in lactic acid buffer. (b) Celecoxib in the same solution and pH, in 1 wt % beta-casein at protein:drug molar ratio of 1:0.5. Note the significant decrease in the size upon the complexation with the protein. The same amount of drug is present in a and b.

Figure 12:
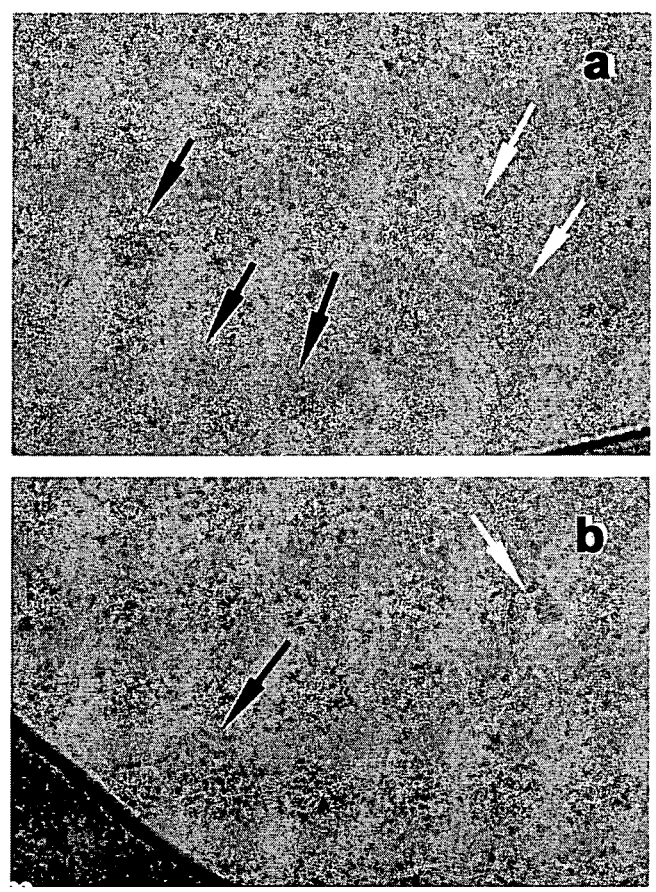
FIG. 12: Cryo-TEM images of celecoxib loaded into beta-casein micelles, in Hepes buffer (pH 6.8). White and black arrows point to mixed protein-drug micelles. Bar=100 nm. Protein concentration is 0.5 wt %, protein-to-drug ratio is 1:1.

FIG. 12 features cryo-TEM images of celecoxib loaded into beta-casein micelles, in hepes buffer (pH 7.1). White and black arrows point to mixed protein-drug micelles. Bar=100 nm. The cryo-TEM samples were prepared by preparing a thin liquid sample and plunging it into liquid ethane at its freezing temperature, forming a vitrified sample. The vitrified sample was transferred to liquid nitrogen and examined at cryogenic temperatures revealing the structures at their native state. The tested protein concentration was 0.5 wt %, and the protein-to-drug ratio was 1:1.

EXAMPLE 10

Representative results with budesonide in acidic and neutral pH: Budesonide is a glucocorticoid steroid for the treatment of asthma, non-infectious rhinitis (including hay fever and other allergies), and for treatment and prevention of nasal polyposis. Additionally, it is used for inflammatory bowel disease. With regard to the present invention, it is an example of a non-chemotherapeutic agent.

Figure 13A:
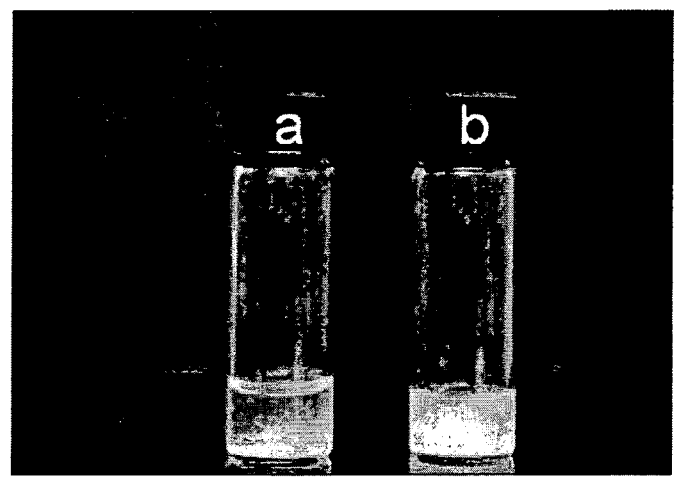
FIG. 13: Photographs of budesonide in lactic acid (a) and in 2% beta-casein (b) protein-to-drug ratio is 1:1.
Figure 13B:
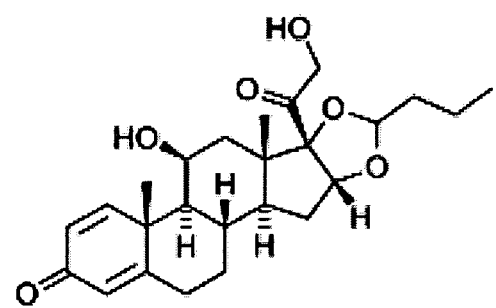

FIG. 13A shows photographs of budesonide in lactic acid (a) and in 2% beta-casein (b); in both cases the protein-to-drug ratio is 1:1. The suspension containing the loaded vehicles is stable over long times. FIG. 13B shows the chemical structure of budesonide.

Figure 14:
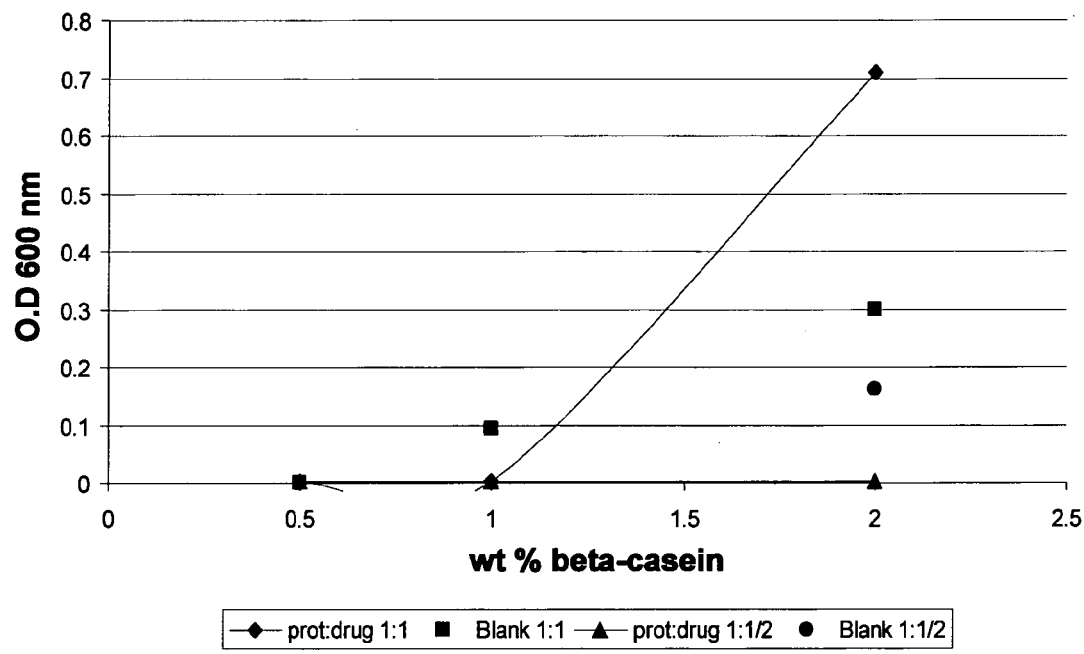
FIG. 14: Variation of the turbidity of beta-casein/budesonide dispersions (lactic acid solution, pH 2.6). Protein concentration is between 0.5 wt % and 2 wt %. Protein-to-drug molar ratio was 1:0.5 and 1:1.

FIG. 14 shows the variation of the turbidity of beta-casein/budesonide dispersions (lactic acid solution, pH 2.6). The drug solution is more transparent because the drug being immiscible is precipitating out of the solution. Upon entrapment in the beta-casein complexes a stable suspension is formed. The protein concentration was varied between 0.5 wt % and 2 wt %. Protein-to-drug molar ratio was 1:05 and 1:1.

Figure 15:
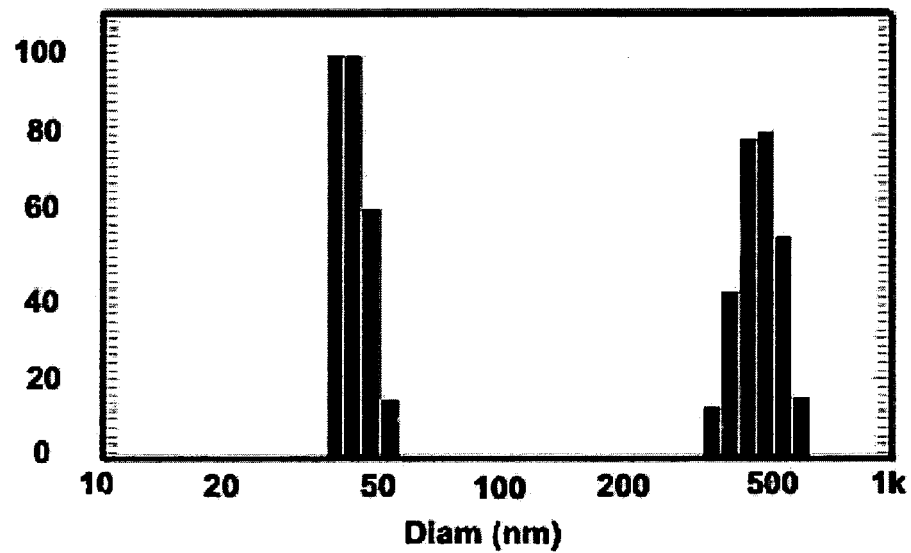
FIG. 15: DLS data of budesonide in lactic acid solution containing 1 wt % beta-casein, 1:2 protein-to-drug ratio.

FIG. 15 shows the DLS data of budesonide in lactic acid solution containing 1 wt % beta-casein, 1:2 protein-to-drug ratio. Two distinct populations may be seen: swollen micelles with characteristic diameter of 40-60 nm, and large complexes of 0.3-0.5 micron in size. Larger assemblies that can be seen by light microscopy were excluded from this analysis. The small assemblies are swollen mixed micelles. Note they are bigger than those found with Celecoxib. The second population relates to drug crystals coated by the assembled protein, as seen by TEM methods (cryo-TEM and FF-TEM).

Figure 16:
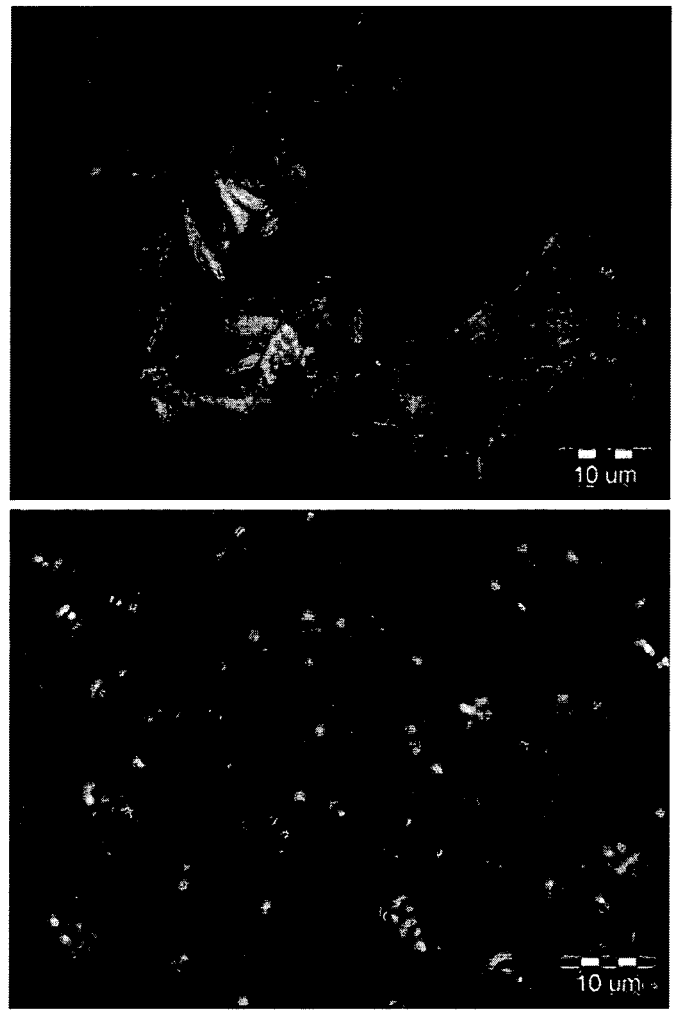
FIG. 16: Light microscopy images at pH 2.6 showing (a) budesonide structures in lactic acid buffer, and (b) budesonide-protein structures at the same solution and pH. Beta-casein is 2 wt %, protein:drug molar ratio of 1:4 (mole ratio).

FIG. 16 shows light microscopy images at pH 2.6 showing (a) budesonide structures in lactic acid buffer, and (b) budesonide-protein structures at the same solution and pH. Beta-casein is 2 wt %, protein:drug molar ratio of 1:4 (mole ratio). Note the significant decrease in the size of the complexes upon interaction with the protein. The size of the complexes is below 1 micron, as confirmed by DLS and light microscopy. Optics effects cause the complexes to appear bigger in size and hollow.

Figure 17:
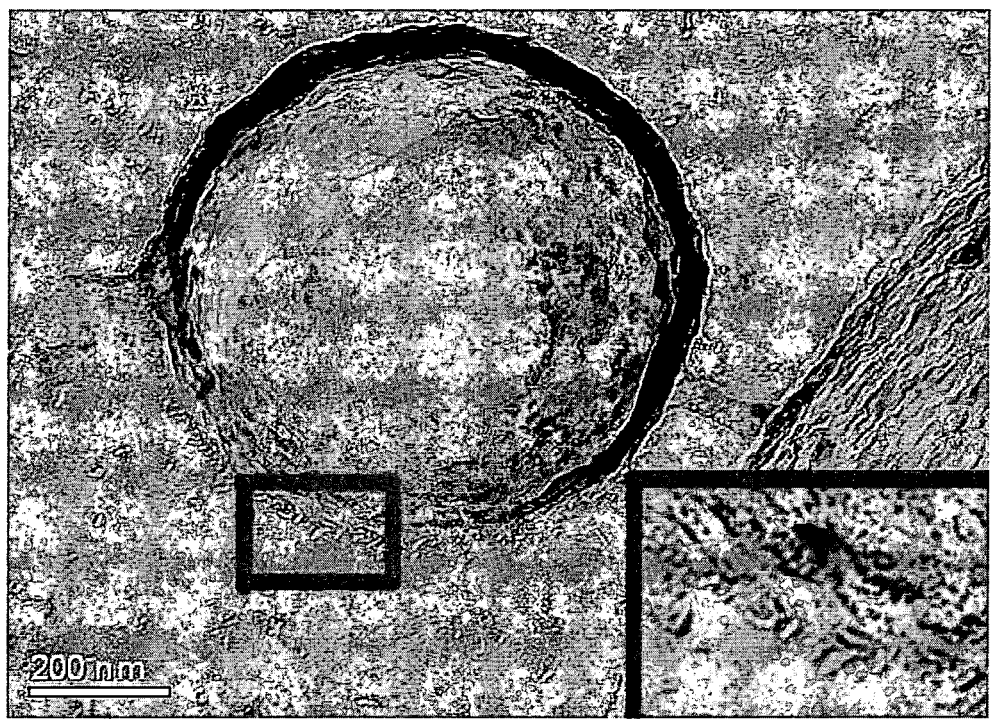
FIG. 17: Freeze-fracture TEM image showing beta-casein/budesonide complex in lactic acid solution at pH 2.6. 2 wt % protein, 1:2 protein-to-drug ratio.

FIG. 17 shows a freeze-fracture TEM image showing beta-casein/budesonide complex, with additional beta-casein micelles and molecules at the surface. (Lactic acid, pH 2.6). The complex size is ~0.5 micron, in agreement with the DLS data. The micelles feature 2 wt % protein, 1:2 protein-to-drug ratio.

Figure 18:
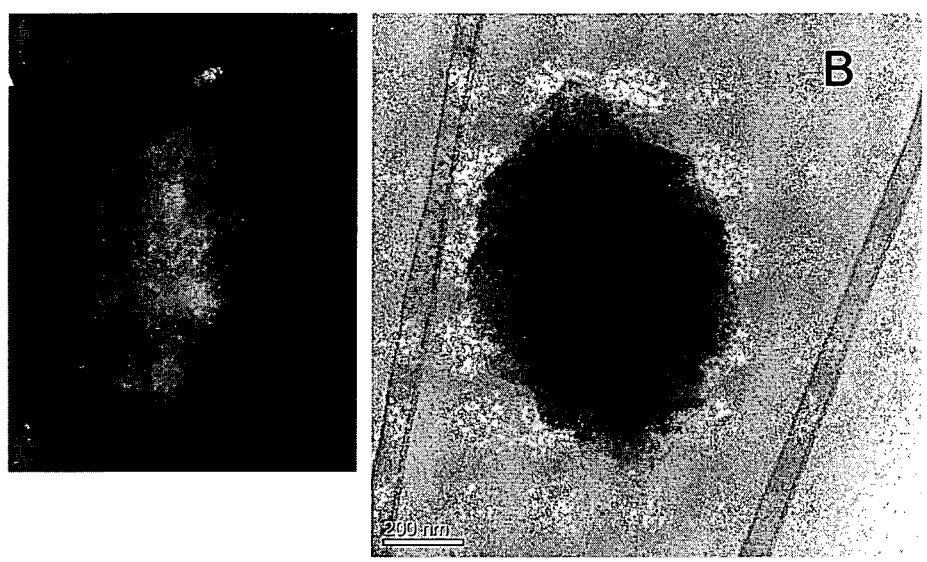
FIG. 18: Negative-stain (A) and cryo-TEM (B) images showing the β-casein/budesonide complexes. 2 wt % protein, 1:2 protein-to-drug ratio.

FIG. 18 shows a negative-stain (left) and cryo-TEM (right) images showing the /beta-casein/budesonide complexes. Again the micelles feature 2 wt % protein, 1:2 protein-to-drug ratio.

Figure 19:
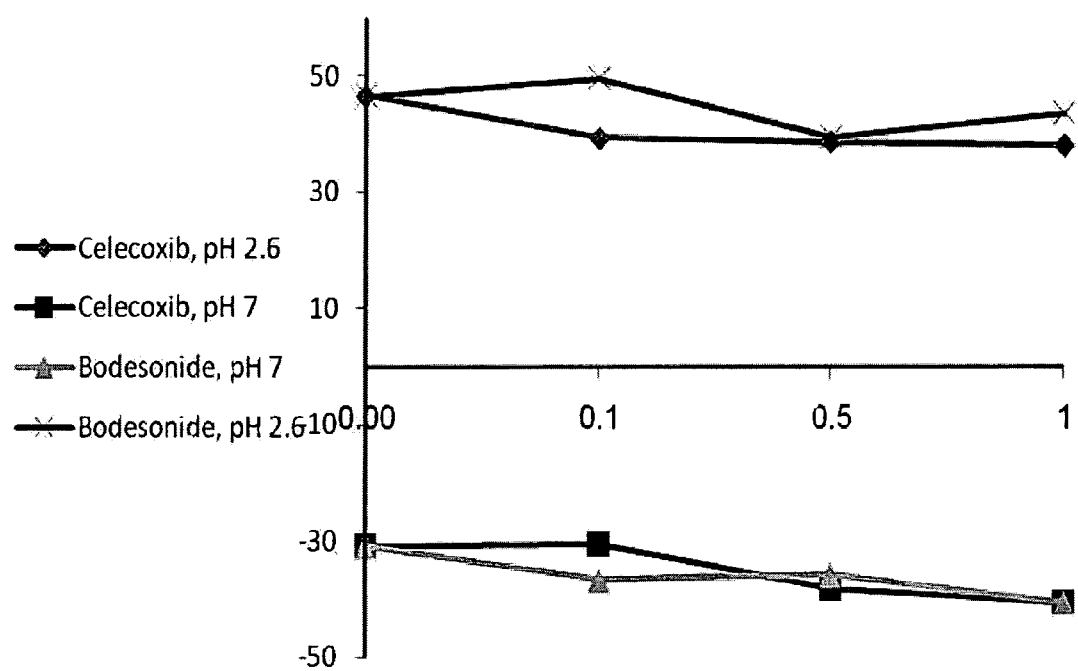
FIG. 19: Plot of the zeta-potential of Celecoxib and budesonide in β-casein, at acidic and neutral pH environments. Protein concentration is 0.1 wt %, protein-to-drug ratio is 1:1

FIG. 19 shows the plot of the zeta-potential of Celecoxib and budesonide in beta-casein, at the two pH environments studied. The figure shows that the protein electrostatic characteristics are dominant and are not drug dependent. The micelles feature a protein concentration of 0.1 wt %; the protein-to-drug ratio is 1:1. The term "zeta potential" refers to electrokinetic potential in colloidal systems, which is the difference in potential between the dispersion medium and the stationary layer of fluid attached to the dispersed particle (all particles feature such a stationary layer of fluid at the interface with the surrounding medium). The fact that the protein electrostatic characteristics are dominant further strengthens the utility of the present invention as being suitable for a wide variety of therapeutic agents.

EXAMPLE 11

Representative results with MPS: Methylprednisolone sodium succinate (MPS) is a synthetic corticosteroid used in severe conditions to reduce inflammation. It is therefore used to treat inflammatory disorders including but not limited to asthma; arthritis; severe allergic reactions; Crohn's disease; and systemic lupus erythematosus. It can be used to decrease fluid retention and swelling in the brain (cerebral edema) due to a brain tumor. It is also used to suppress the immune system in organ transplantation. MPS is widely used in the management of renal transplantation. To use MPS without severe adverse reactions, lower administration rates and dosages are very important, and may optionally be achieved with the micelles of the present invention. With regard to the present invention, it is an example of a non-chemotherapeutic agent.

Figure 20A:
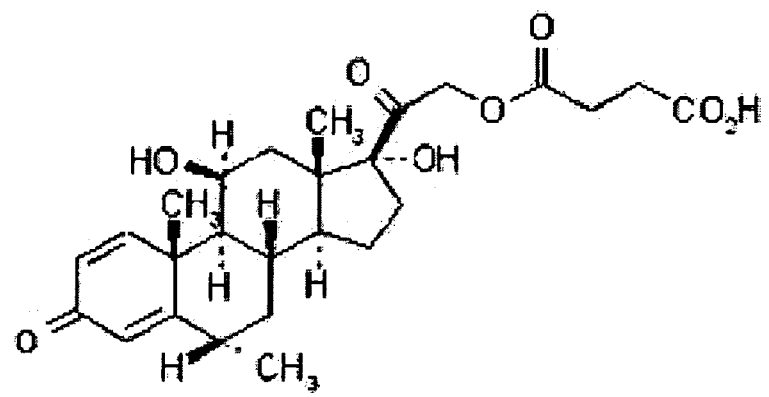
FIG. 20: DLS data of MPS in lactic acid solution containing 1 wt % β-casein, protein-to-drug ratio is 1:2
Figure 20B:
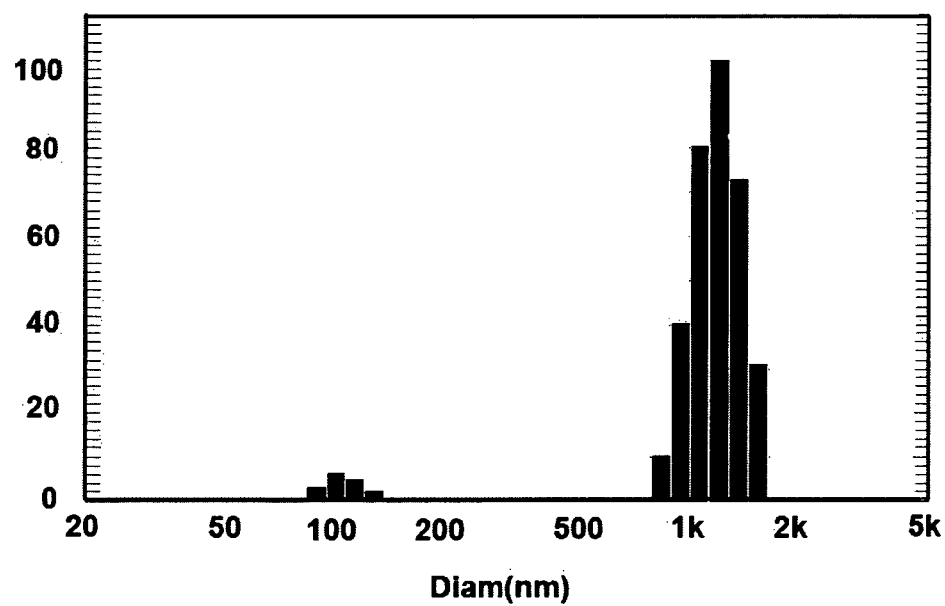

FIG. 20A shows the chemical structure of MPS. FIG. 20B shows DLS data of MPS in lactic acid solution containing 1 wt % beta-casein, protein-to-drug ratio is 1:2 Note coexistence of two populations: mixed protein-drug complexes that are about 90-120 nm, and larger complexes of ~0.5-1.5 micron.

Figure 21:
FIG. 21: Light micrsocpy images of MPS aggregates in the absence (A) and the presence of in 2% β-casein (B) in lactic acid solution (pH 2.6). protein-to-drug ratio is 1:2

FIG. 21 shows light microscopy images of MPS aggregates in the absence (A) and the presence of in 2% beta-casein (B); lactic acid solution (pH 2.6). The mixed assemblies are much smaller in size, indicating clearly the interaction between the protein and the drug. The protein-to-drug ratio is 1:2.

EXAMPLE 12

Representative results with Sodium clodronate: Sodium clodronate reduces bone destruction that could result in bone pain and fractures. It is also used to bring down high calcium blood levels to normal as well as maintain normal calcium blood levels. In some cases, it is used as an adjunct to cancer treatment, to prevent bone weakening and fractures. With regard to the present invention, it is an example of a non-chemotherapeutic agent.

Figure 22:
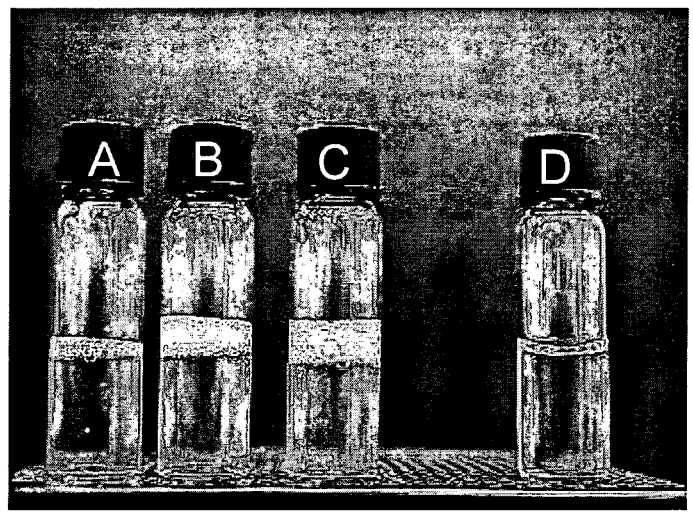
FIG. 22: Photographs of Sodium clodronate in lactic acid (right) and in β-casein (a). Left to right: increasing protein concentration equal to 0.5%, 1% and 2%, at constant 1:2 protein:drug ratio.

FIG. 22 features photographs of Sodium clodronate in lactic acid (D) and in beta-casein (A-C). Left to right: increasing protein concentration equal to 0.5% (A), 1% (B) and 2% (C), at constant 1:2 protein:drug ratio. All suspensions were transparent.

Figure 23:
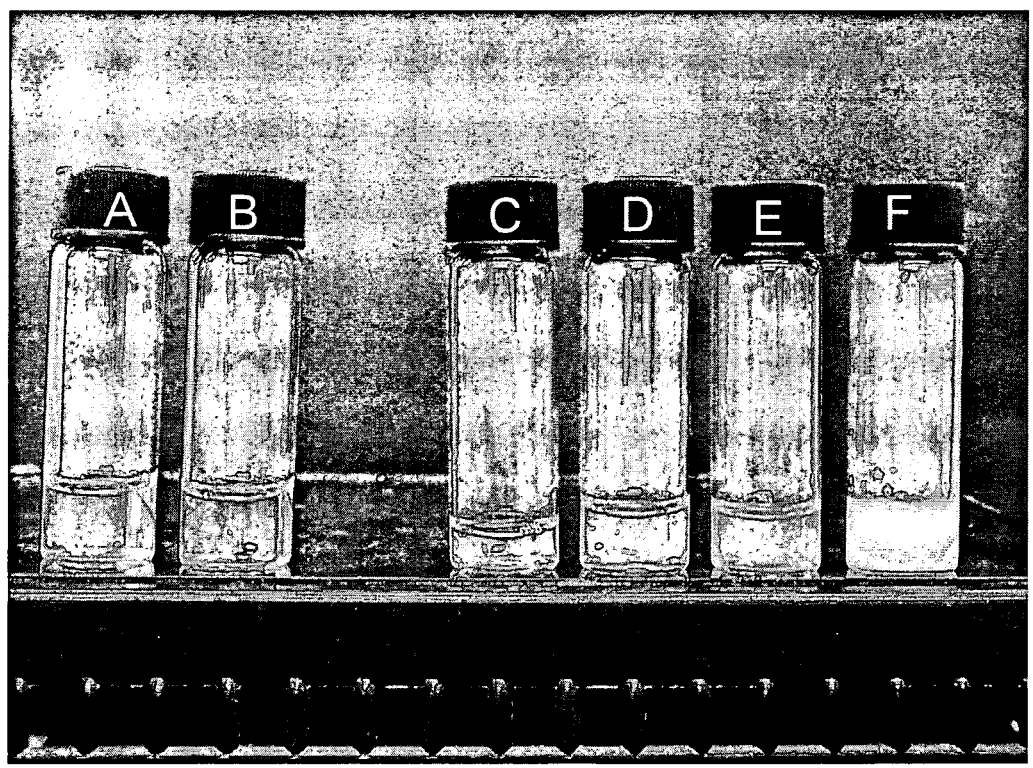
FIG. 23: Photographs of Sodium clodronate and beta-casein solutions with increasing ratios of Sodium clodronate to beta-casein in lactic acid (pH 2.6). A: Sodium clodronate only; B: beta-casein only; C: 1:1; D: 2:1; E: 4:1; F: 10:1; beta-casein concentration was equal to 2% by weight.

FIG. 23 features photographs of Sodium clodronate and beta-casein solutions with increasing ratios of Sodium clodronate to beta-casein in lactic acid (pH 2.6). A: Sodium clodronate only; B: beta-casein only; C: 1:1; D: 2:1; E: 4:1; F: 10:1; beta-casein concentration equal to 2% by weight.

Figure 24:
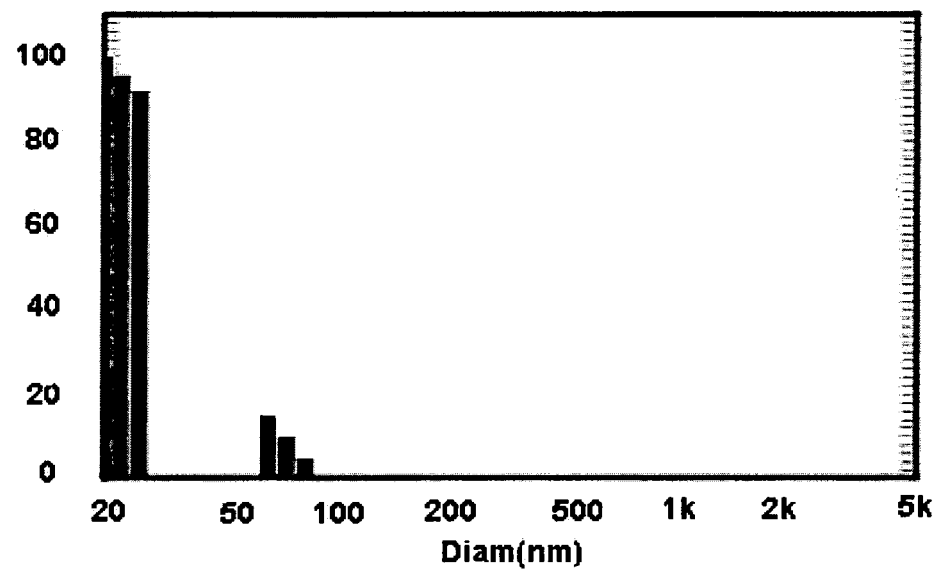
FIG. 24: DLS data of Sodium clodronate in lactic acid solution at pH 2.6 containing 2 wt % β-casein; the protein-to-drug ratio is 1:2.

FIG. 24 features DLS data showing two small populations of micelles. The smaller population is probably of empty micelles. The aggregates at the 69-90 nm in size are likely micelles loaded with Sodium clodronate. The protein concentration is 2%, and the protein-to-drug ratio is 1:2.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

The invention claimed is:

1. A composition comprising micelles and at least one therapeutic agent, wherein the micelles are a carrier for the therapeutic agent, and wherein said micelles are not held together by calcium-phosphate bridges and are selected from the group consisting of micelles comprising denatured isolated beta-casein prepared at a pH value at least one unit below the pI of beta-casein, wherein the isolated beta-casein is at least about 70% of the total casein and micelles comprising isolated beta-casein prepared at neutral pH, wherein the isolated beta-casein is at least about 70% of the total casein.

2. The composition of claim 1, wherein the isolated beta-casein is at least about 80% of the total casein.

3. The composition of claim 2, wherein the isolated beta-casein of said micelles is at least about 90% of the total casein.

4. The composition of claim 2, wherein the isolated beta-casein of said micelles is at least about 95% of the total casein.

5. The composition of claim 1, wherein said micelles comprise denatured isolated beta-casein and wherein said denatured isolated beta-casein comprises beta-casein prepared at a pH value at least two units below the pI of beta-casein.

6. The composition of claim 1, wherein the beta casein to therapeutic agent molar ratio is in the range of 1:1 to 1:10.

7. The composition of claim 1, wherein said micelles are stable at a temperature in a range of at least from about 10C. to at least about 450C.

8. The composition of claim 1, wherein said therapeutic agent comprises an agent having at least one characteristic selected from the group consisting of hydrophobic, poorly absorbed through a mucosal membrane, non-stable in the gastrointestinal tract or any part thereof, insoluble in an aqueous solution and/or at body pH values, and/or pH sensitive.

9. The composition of claim 8, wherein said therapeutic agent is selected from the group consisting of an anti-resorptive agent, a steroid, a NSAID (non-steroidal anti-inflammatory drug) and a chemotherapeutic agent.

10. The composition of claim 9, wherein said anti-resorptive comprises sodium clodronate.

11. The composition of claim 9, wherein said steroid comprises one or more of budesonide or methylprednisolone hemisuccinate sodium salt (MPS).

12. The composition of claim 9, wherein said NSAID comprises celecoxib.

13. The composition of claim 9, wherein said therapeutic agent does not comprise an anti-cancer chemotherapeutic agent.

14. The composition of claim 9, wherein said therapeutic agent comprises an adjunct therapy for cancer therapy.

15. The composition of claim 1, wherein said micelles have a diameter selected from the group consisting of below about 300 nm, below about 200 nm and below about 100 nm.

16. A pharmaceutical composition comprising the micelles according to claim 1.

17. A method for treating a mucosal membrane, comprising administering the composition of claim 1 to a mucosal membrane.

18. The method of claim 17, wherein said mucosal membrane is selected from the group consisting of oral, gastrointestinal, nasal, rectal and vaginal.

19. A method for treating cancer, comprising administering to a patient in need thereof, the composition of claim 1, wherein the at least one therapeutic agent is used as an adjunct to cancer therapy.

20. A method for treating a local and/or systemic condition, comprising administering the composition of claim 1 to the gastrointestinal tract in a patient in need thereof, wherein the at least one therapeutic agent is effective to treat the local and/or systemic condition.

21. The method of claim 20, wherein said local condition comprises an inflammatory condition.

* * * * *